(12) United States Patent
Figuly et al.

(10) Patent No.: US 7,794,755 B2
(45) Date of Patent: Sep. 14, 2010

(54) PROCESS FOR PREPARATION OF SWELLABLE AND DEFORMABLE MICROSPHERES

(75) Inventors: Garret D. Figuly, Wilmington, DE (US); Surbhi Mahajan, Wilmington, DE (US); Rinaldo S. Schiffino, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 668 days.

(21) Appl. No.: 11/784,066

(22) Filed: Apr. 5, 2007

(65) Prior Publication Data

US 2007/0237956 A1 Oct. 11, 2007

Related U.S. Application Data

(60) Provisional application No. 60/791,084, filed on Apr. 11, 2006.

(51) Int. Cl.
- A61K 9/14 (2006.01)
- A61K 9/16 (2006.01)
- A61K 51/02 (2006.01)
- C08F 2/20 (2006.01)
- C08F 2/44 (2006.01)

(52) U.S. Cl. ............. 424/501; 424/1.29; 424/489; 424/494; 524/848; 524/849

(58) Field of Classification Search .............. None
See application file for complete search history.

(56) References Cited

U.S. PATENT DOCUMENTS

| | | | |
|---|---|---|---|
| 3,615,972 A | 10/1971 | Morehouse, Jr. et al. | |
| 4,446,261 A | 5/1984 | Yamasaki et al. | |
| 4,935,456 A | 6/1990 | Huang et al. | |
| 5,716,981 A | 2/1998 | Hunter et al. | |
| 6,218,440 B1 * | 4/2001 | Kitagawa ................ | 521/56 |
| 6,436,424 B1 | 8/2002 | Vogel et al. | |
| 6,511,744 B2 * | 1/2003 | Centner et al. ........ | 428/355 EN |
| 6,590,094 B2 * | 7/2003 | Karlou-Eyrisch et al. .. | 536/25.4 |
| 6,790,456 B2 | 9/2004 | Vogel et al. | |
| 2003/0093157 A1 * | 5/2003 | Casares et al. .......... | 623/23.73 |
| 2003/0211165 A1 | 11/2003 | Vogel et al. | |
| 2003/0212022 A1 | 11/2003 | Vogel et al. | |
| 2006/0009674 A1 | 1/2006 | Miller | |
| 2006/0024371 A1 | 2/2006 | Hnojewyj et al. | |
| 2006/0039896 A1 | 2/2006 | Kleinsek et al. | |

FOREIGN PATENT DOCUMENTS

| | | |
|---|---|---|
| DE | 10 2004 042948 A1 | 3/2006 |
| EP | 0349240 A2 | 1/1998 |
| JP | 2004/041955 A1 | 5/2004 |
| WO | WO 98/33825 A | 8/1998 |
| WO | WO 99/12577 | 3/1999 |
| WO | WO 99/34829 | 7/1999 |
| WO | WO 00/23054 | 4/2000 |
| WO | WO 01/70289 A2 | 9/2001 |
| WO | WO 01/72281 A2 | 10/2001 |
| WO | WO 03/094930 A1 | 11/2003 |
| WO | WO 2004/073688 A1 | 9/2004 |

OTHER PUBLICATIONS

Water soluble Azo initiators (Wako Pure Chemical Industries Ltd.), 2006.*
Thanoo et al. (Biomaterials 1990, 11, 477-481).*
Yao et al., A new artery embolism substance—The characteristic and the embolism effect of high water absorptivity polymer (SAP-Microsphere), Osaka University Medical Department Radiology, Nippon Igaku Hoshasen Gakkai Zasshi 1996, 56, 19-24.

* cited by examiner

*Primary Examiner*—Ernst V Arnold
*Assistant Examiner*—Jessica Kassa

(57) ABSTRACT

A process for producing microspheres was developed that provides microspheres with new combined properties of high density, low fracture, high swell capacity, rapid swell, and deformability following swell. The process is reliable and high yielding, and makes use of a low temperature azo initiator and a small molecule chlorinated solvent as the organic phase. The microsphere preparation made using the process is particularly useful in medical treatments such as embolization.

23 Claims, 10 Drawing Sheets

T = 0 sec

T = 4 sec

T = 14 sec

T = 0 sec

T = 4 sec

T = 14 sec

PROCESS FOR PREPARATION OF SWELLABLE AND DEFORMABLE MICROSPHERES

CROSS-REFERENCE TO RELATED APPLICATION

This application claims priority under 35 U.S.C. §119 from U.S. Provisional Application Ser. No. 60/791,084, filed Apr. 11, 2006.

FIELD OF INVENTION

The present invention relates to hydrogel microspheres, including a process for preparing swellable/deformable microspheres and a preparation of swellable/deformable microspheres.

BACKGROUND OF THE INVENTION

There is a need for microspheres with properties that are advantageous for many types of applications, including medical applications. Microspheres with high density, yet a large capacity to swell in an aqueous environment, would be useful for absorption applications such as small-scale spill control and for delivery applications in which they would carry and release active ingredients such as fertilizers, herbicides, pesticides, cosmetics, shampoos, and medications. Microspheres with additional properties of durability and deformability would provide a valuable material for introduction into animals, including humans, for applications such as tissue augmentation, void filling, wound treatment, and embolization. Tissue augmentation involves introduction of materials in a collapsed area to provide a filling function, such as the treatment of scars or wrinkles. Void filling involves introduction of materials into an empty space, such as one created by removal of a tissue mass. Wound treatment involves introduction of materials to stop bleeding, provide padding, deliver medication, and absorb fluids. Such materials are useful especially in emergency situations including accidents and military operations. Embolization treatment involves the introduction of a material into the vasculature in order to block the blood flow in a particular region, and may be used to treat non-cancerous tumors, such as uterine fibroids, and cancerous tumors, as well as to control bleeding caused by conditions such as stomach ulcers, aneurysms, and injury. Blockage may be desired in the case of arteriovenous malformation (AVM), where abnormal connections occur between arteries and veins. Additionally, blockage may be desired for pre-surgical control of blood flow.

Hydrogel microspheres have been produced and used in tissue augmentation and embolization treatments. Properties of a sample of microspheres are generally related not only to the materials used in microsphere preparation, but also to the process by which the microspheres are prepared. U.S. Pat. No. 6,218,440 discloses a process for preparing hydrogel microspheres in which an emulsion is first prepared, and then this emulsion is suspended in an oil medium. Microspheres formed by this process have many cavities joined by interconnecting pores, with cavities at the interior of the material in communication with the surface, since a porous crosslinked hydrophilic polymeric material is produced.

U.S. Pat. No. 4,446,261 discloses a process for making hydrogel microspheres which includes dispersing a solution containing monomer, crosslinking agent and initiator in a dispersion medium consisting of hydrocarbons having from 6 to 10 carbon atoms or halogenated aromatic hydrocarbons, with a protective colloid dissolved in this oil material.

U.S. Pat. No. 6,436,424 discloses microspheres suitable for dermal augmentation that are said to swell upon contacting physiological fluids at the injection site to up to four times the average diameter of the microspheres prior to injection. These hydrogel microspheres are said to be made by standard methods of polymerization and microsphere preparation described in the art. The microspheres described in U.S. Pat. No. 6,790,456 are the same as those described in U.S. Pat. No. 6,436,424.

JP1994056676A discloses a suspension used for embolization containing lipidic contrast agent and highly water absorbent hydrogel particles of vinyl alcohol and sodium acrylate polymer that are approximately 1.0 mm in diameter or less.

There remains a need for a new process to prepare microspheres which is simple, consistent, and produces microspheres with valuable properties.

SUMMARY OF THE INVENTION

One aspect of the present invention is a process for making a microsphere preparation including the following steps:
a) forming a first solution comprising:
(i) water;
(ii) at least one water miscible monomer selected from the group consisting of acrylic acid, methacrylic acid, salts of acrylic acid and methacrylic acid, acrylamide, methacrylamide, N-substituted acrylamides, N-substituted methacrylamides, 2-acryloylethane-sulfonic acid, 2-methacryloylethane-sulfonic acid, salts of 2-acryloylethane-sulfonic acid and 2-methacryloylethane-sulfonic acid, styrene-sulfonic acid, salts of styrene-sulfonic acid, 2-hydroxyethyl acrylate, and 2-hydroxyethyl methacrylate, provided that:
(A) if said monomer is acrylamide, methacrylamide, N-substituted acrylamides, 2-hydroxyethyl acrylate, or 2-hydroxyethyl methacrylate, said monomer is used in combination with at least one other monomer selected from subgroup 1 consisting of: acrylic acid, methacrylic acid, salts of acrylic acid and methacrylic acid, 2-acryloylethane-sulfonic acid, 2-methacryloylethane-sulfonic acid, salts of 2-acryloylethane-sulfonic acid and 2-methacryloylethane-sulfonic acid, styrene-sulfonic acid, and salts of styrene-sulfonic acid;
(B) if said first solution contains at least one monomer from subgroup 2 consisting of acrylic acid, methacrylic acid, salts of acrylic acid and methacrylic acid, acrylamide, methacrylamide, N-substituted acrylamides, N-substituted methacrylamides, 2-hydroxyethyl acrylate, and 2-hydroxyethyl methacrylate, but does not contain a monomer selected from subgroup 3 consisting of 2-acryloylethane-sulfonic acid, 2-methacryloylethane-sulfonic acid, salts of 2-acryloylethane-sulfonic acid and 2-methacryloylethane-sulfonic acid, styrene-sulfonic acid, and salts of styrene-sulfonic acid, then the pH of the first solution is at least about 3; or
(C) if said first solution contains at least one monomer from subgroup 3 consisting of 2-acryloylethane-sulfonic acid, 2-methacryloylethane-sulfonic acid, salts of 2-acryloylethane-sulfonic acid and 2-methacryloylethane-sulfonic acid, styrene-sulfonic acid, and salts of styrene-sulfonic acid, then the pH of the first solution is less than about 3;

(iii) a crosslinking agent that is miscible in the first solution in less than or equal to about 5 Mol %, relative to total moles of monomer and crosslinking agent, said crosslinking agent being selected from the group consisting of N,N'-methylene-bis-acrylamide, N,N'-methylene-bis-methacrylamide, N-methylolacrylamide, N-methylolmethacrylamide, glycidyl acrylate, glycidyl methacrylate, polyethylene glycol diacrylate, polyethylene glycol dimethacrylate, polyvalent metal salts of acrylic acid and methacrylic acid, divinyl benzene phosphoacrylates, divinylbenzene, divinylphenylphosphine, divinyl sulfone, 1,3-divinyltetramethyldisiloxane, 3,9-divinyl-2,4,8,10-tetraoxaspiro[5,5]undecane, phosphomethacrylates, ethylene glycol diglycidyl ether, glycerin triglycidyl ether, glycerin diglycidyl ether, and polyethylene glycol diglycidyl ether;

(iv) a water soluble protecting colloid;

(v) an emulsifier; and (vi) a low temperature aqueous soluble azo initiator;

b) forming a second solution comprising at least one substantially chlorinated hydrocarbon of less than 6 carbon units, provided that the chlorinated hydrocarbon is not a halogenated aromatic hydrocarbon, and an organic soluble protecting colloid;

c) forming a first suspension with agitation comprising the first and second solutions at a temperature below the initiation temperature of the azo initiator of (a);

d) increasing the temperature of the agitating first suspension to a temperature at which the low temperature aqueous soluble azo initiator is activated;

e) agitating the first suspension until it forms a second suspension comprising a gelatinous precipitate suspended in an organic liquid phase, wherein microspheres are formed;

f) allowing the second suspension to cool to a temperature that is at or below about 30° C. while agitating the second suspension;

g) washing the second suspension at least once with a dehydrating solvent wherein water is removed from the microspheres forming a microsphere preparation; and h) recovering the microsphere preparation.

Another aspect of the present invention is a preparation of microspheres prepared by the steps of the present process.

Another aspect of the present invention is a suspension of microspheres comprising microspheres prepared by the steps of the present process.

A further aspect of the present invention is a kit containing a quantity of the present microsphere preparation.

DETAILED DESCRIPTION

Figure 1A:
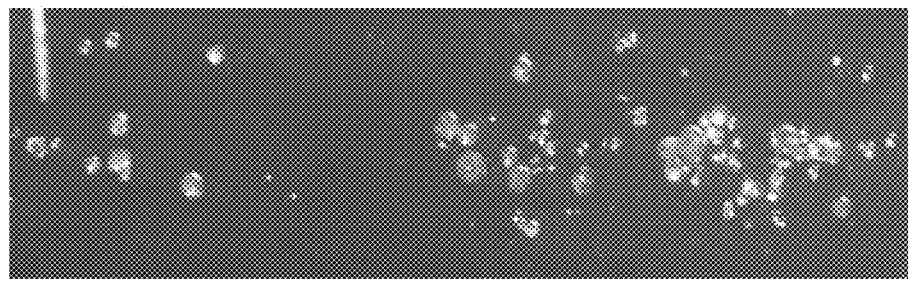
FIG. 1 shows a time course of swelling in water of microspheres prepared by the present process: A) no water added, B) 4 sec after water contact, C) 14 sec after water contact, with the microsphere boundaries enhanced.

The present invention provides a process for preparing microspheres which is simple, consistent, and produces microspheres with valuable properties at a high yield. The resulting microspheres have properties of general consistency in size and shape, high density, low fracture, high swell capacity, rapid swell, and deformability following swell. The process makes use of a water soluble, low temperature-active azo initiator in an aqueous solution of monomer, crosslinking agent, and emulsifier. A chlorinated organic medium is used in forming a suspension with the aqueous solution. The aqueous solution and organic medium both additionally include protecting colloids. The aqueous solution and organic medium, as well as the mixture of the two, are initially held below the initiation temperature of the azo initiator. The organic medium, which may comprise a chloroform and methylene chloride mixture, should have a high enough boiling temperature that the aqueous soluble azo initiator can be activated to cause polymerization producing microspheres.

The present invention is also directed in another embodiment toward a preparation of microspheres that is produced according to the process of the invention. The microspheres have properties that make them highly useful in, for example, medical applications such as embolization, tissue augmentation and wound treatment.

When an amount, concentration, or other value or parameter is recited herein as either a range, preferred range or a list of upper preferable values and lower preferable values, the recited amount, concentration, or other value or parameter is intended to include all ranges formed from any pair of any upper range limit or preferred value and any lower range limit or preferred value, regardless of whether such ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The following definitions and abbreviations are to be used for the interpretation of the claims and the specification.

The term "microspheres" or "microsphere" refers to either a population of micron size particles, or an individual particle, depending upon the context in which the word is used, which has a high sphericity measurement. The sphericity measurement of a population of microspheres may be in the range of about 80% to about 100%, with 95% being typical. The microspheres are substantially spherical, although a microsphere population may include some individual particles that have a lower sphericity measurement.

The term "miscible" refers to mixing of two liquids without separation of two phases. In addition, a solid is miscible if a solution made with the solid is miscible with another liquid. Specifically, a liquid monomer may itself be miscible with water. A solid monomer is water miscible when an aqueous solution prepared with the solid monomer can be mixed with water without having a separation of two phases.

The term "substantially chlorinated hydrocarbon" refers to a hydrocarbon that is from 50% to fully chlorinated. Carbon tetrachloride is an example of such a hydrocarbon.

The term "slurry" refers to a composition that is a particulate material in a liquid.

The terms "first suspension" and "second suspension" refer to suspensions formed during the process of preparing microspheres that is described herein.

The term "embolization suspension" refers to a suspension that contains microspheres and is administered using a catheter and/or needle for embolization treatment.

The term "deformable" refers to the property of being able to change shape in response to an external pressure. Microspheres are deformable if they do not retain their shape when they are swelled, following uptake of an aqueous medium, and are subjected to pressure.

The term "substantially nonexpendable tubing" refers to tubing that has no visually observable expansion under the testing conditions in which it is used.

The term "swell-control medium" refers to a medium that controls the swell of microspheres, prepared by the present process, such that there is little or no swell. A small amount of swell may occur. However, full swell that is about 50× or more than the original volume does not occur.

Monomer and Crosslinking Agent

Monomers that may be used in the present process for preparing microspheres are water miscible monomers including, but not limited to, acrylic acid, methacrylic acid, salts (such as sodium and ammonium) of acrylic acid and methacrylic acid, acrylamide, methacrylamide, N-substituted acrylamides, N-substituted methacrylamides, 2-acryloylethane-sulfonic acid, 2-methacryloylethane-sulfonic acid, salts of 2-acryloylethane-sulfonic acid and 2-methacryloylethane-sulfonic acid, styrene-sulfonic acid, salts of styrene-sulfonic acid, 2-hydroxyethyl acrylate, and 2-hydroxyethyl methacrylate. Monomers may be used singly or in combinations as co-monomers. Monomers that perform well as single monomer components (subgroup 1) include acrylic acid, methacrylic acid, salts (such as sodium and ammonium) of acrylic acid and methacrylic acid, 2-acryloylethane-sulfonic acid, 2-methacryloylethane-sulfonic acid, salts of 2-acryloylethane-sulfonic acid and 2-methacryloylethane-sulfonic acid, styrene-sulfonic acid, and salts of styrene-sulfonic acid. Preferably, the following monomers are used as co-monomers with at least one of the monomers from subgroup 1: acrylamide, methacrylamide, N-substituted acrylamides, N-substituted methacrylamides, 2-hydroxyethyl acrylate, and 2-hydroxyethyl ethacrylate. Most useful in producing microspheres for medical applications are monomers having biocompatibility such as acrylic acid, methacrylic acid, salts of acrylic acid and methacrylic acid, 2-hydroxyethyl acrylate and 2-hydroxyethyl methacrylate, and combinations thereof. In one embodiment the monomer is a combination comprising acrylic acid and at least one monomer from the group of sodium acrylate, 2-hydroxyethyl methacrylate, 2-hydroxyethyl acrylate, styrene sulfonic acid, and the sodium salt of styrene sulfonic acid. In another embodiment, the monomer is styrene sulfonic acid or a combination comprising styrene sulfonic acid and the sodium salt of styrene sulfonic acid.

Many of these monomers are liquids which are miscible with water. For monomers that are solids, an aqueous solution of the monomer may be prepared, and this monomer solution is miscible with water. Acid monomers and salts of monomers may be combined to adjust the pH of a monomer solution. It is particularly useful to partially neutralize an acid monomer, thereby providing a mixture of acid monomer and monomer salt. Acid monomers that may be used are, for example, acrylic acid, methacrylic acid, 2-acryloylethane-sulfonic acid, 2-methacryloylethane-sulfonic acid, styrene-sulfonic acid, and combinations thereof. A monomer prior to partial neutralization is referred to as an initial monomer. An acid monomer is typically partially neutralized using a base. Suitable bases include, but are not limited to, sodium hydroxide, potassium hydroxide, ammonium hydroxide, lithium hydroxide and combinations thereof. Bases containing divalent cations, such as calcium hydroxide and barium hydroxide may also be used; however, they are preferably used in combination with a base containing monovalent cations because divalent cations have a strong tendency to induce ionic crosslinking, which could severely alter the desirable properties of the microspheres. For some applications it may be desirable to substitute a portion of the base with barium hydroxide ($Ba(OH)_2$) to introduce a radio-opaque element, which makes the resulting microspheres amenable to x-ray imaging. Barium hydroxide may be used in a ratio of up to about 1:1 by weight of $Ba(OH)_2$ to NaOH, to produce a combination salt that includes barium salt. Alternatively, a barium monomer salt may be included in a monomer combination.

A crosslinking agent that is miscible with an aqueous monomer solution is copolymerized with the monomer in the present process. Examples of crosslinking agents that may be used include, but are not limited to, N,N'-methylene-bis-acrylamide, N,N'-methylene-bis-methacrylamide, N-methylolacrylamide, N-methylolmethacrylamide, glycidyl acrylate, glycidyl methacrylate, polyethylene glycol diacrylate and polyethylene glycol dimethacrylate (which are most useful with hydrophobic monomers), polyvalent metal salts of acrylic acid and methacrylic acid, divinyl benzene phosphoacrylates, divinylbenzene, divinylphenylphosphine, divinyl sulfone, 1,3-divinyltetramethyldisiloxane, 3,9-divinyl-2,4,8,10-tetraoxaspiro[5,5]undecane, phosphomethacrylates, and polyol polyglycidyl ethers such as ethylene glycol diglycidyl ether, glycerin triglycidyl ether, glycerin diglycidyl ether, and polyethylene glycol diglycidyl ether, and combinations thereof. The amount of crosslinking agent included for copolymerization may vary and is inversely related to the amount of swell capacity in the microspheres produced using the present process. Different amounts of crosslinking agent result in swelling capacities over a range of about 1.5 grams of water per gram of microspheres to over 100 grams of water per gram of microspheres. Generally useful is an amount of crosslinking agent that results in microspheres with a swell capacity of at least about 50 grams of water per gram of microspheres. Particularly useful is an amount of crosslinking agent that results in microspheres with a swell capacity of at least about 70 grams of water per gram of microspheres. The exact amount of crosslinking agent needed will vary depending on the specific agent used and can be readily determined by one skilled in the art. The amount of crosslinking agent is calculated as Mol % (mole percent) based on the sum of the moles of monomer and moles of crosslinking agent. Thus, the Mol % is calculated as moles of crosslinking agent/(moles of monomer+moles of crosslinking agent). For example, 4.0 Mol % of N,N'-methylenebisacrylamide with respect to moles of acrylic acid monomer+sodium acrylate+crosslinking agent produces microspheres with a swell of about 50 grams of water per gram of microspheres, 2.9 Mol % of N,N'-methylenebisacrylamide produces microspheres with a swell of about 70 grams of water per gram of microspheres, and 2.3 Mol % of N,N'-methylenebisacrylamide produces microspheres with a swell of about 107 grams of water per gram of microspheres. Preferably, the Mol % of crosslinking agent is equal to or less than about 5 Mol %, preferably, equal to or less than about 4 Mol %, more preferably about 0.08 Mol % to about 4 Mol %, most preferably about 0.08 Mol % to about 2.3 Mol % relative to total moles of monomer and crosslinking agent. Microspheres with very high swell (i.e., over 250 grams of water per gram of microspheres) can be prepared using a hydrophilic monomer such as sodium acrylate, a low amount of crosslinking agent (e.g., 0.083 Mol % of N,N'-methylenebisacrylamide), with low temperature drying conditions, as described in Example 35 below.

First Solution

A monomer and crosslinking agent as described above are prepared in an aqueous solution, together with additional components, which is herein called the "first solution". The monomer is generally included at about 0.5% to about 30% as weight percent of the first solution. Monomer weight percents of about 15% to about 25% and about 20% to about 25% are particularly useful in the process of the invention. If a combination of monomers is used in the process, the total amount of all the monomers is about 0.5% to about 30%, in addition from about 15% to about 25%, and in addition from about 20% to about 25%, as weight percent of the first solution.

The pH of the first solution may vary and is a factor in the swell capacity of the microspheres prepared in the process of the invention. The useful pH range of the first solution also depends on the particular monomer or combination of monomers used. If the first solution contains at least one monomer from subgroup 2 consisting of acrylic acid, methacrylic acid, salts of acrylic acid and methacrylic acid, acrylamide, methacrylamide, N-substituted acrylamides, N-substituted methacrylamides, 2-hydroxyethyl acrylate, and 2-hydroxyethyl methacrylate, but does not contain a monomer from subgroup 3 consisting of 2-acryloylethane-sulfonic acid, 2-methacryloylethane-sulfonic acid, salts of 2-acryloylethane-sulfonic acid and 2-methacryloylethane-sulfonic acid, styrene-sulfonic acid, and salts of styrene-sulfonic acid, then the pH of the first solution is at least about 3, preferably between about 3.5 and about 10, more preferably between about 5 and about 9, to produce microspheres with a high swell capacity. For example, a mixture of acrylic acid and sodium acrylate at a pH of between about 3.5 and about 10, and a 2 to 5 Mol % of N,N'-methylenebisacrylamide crosslinking agent (with respect to the monomer), when used in the process of the invention, produces microspheres with a swell capacity of at least about 80 grams of water per gram of microspheres. If the first solution contains at least one monomer from subgroup 3 consisting of 2-acryloylethane-sulfonic acid, 2-methacryloylethane-sulfonic acid, salts of 2-acryloylethane-sulfonic acid and 2-methacryloylethane-sulfonic acid, styrene-sulfonic acid, and salts of styrene-sulfonic acid, then the pH of the first solution is less than about 3 to produce highly swellable microspheres (see Examples 36-38).

The pH of the first solution may be adjusted in any number of ways. For example, if the monomer is prepared as a monomer solution, as described above, the pH of the monomer solution will govern the pH of the first solution. In the case of an acid monomer, the pH of the monomer solution is related to the amount of base or monomer salt added to the acidic monomer solution. Alternatively, the pH of the first solution may be adjusted as required by the addition of acid or base after all the components have been added.

Included in the "first solution" is a component that can modify the viscosity of an aqueous solution to provide a surface tension that allows droplet formation in the aqueous/organic suspension that is formed during the present microsphere preparation process. This component is referred to herein as a "protecting colloid". A variety of natural and synthetic compounds that are soluble in aqueous media may be used as a protecting colloid including cellulose derivatives, polyacrylates (such as polyacrylic acid and polymethacrylic acid), polyalkylene glycols such as polyethylene glycol, partially hydrolyzed polyvinyl alcohol and other polyols, guar gum, and agar gum. Particularly useful are cellulose ethers such as methyl cellulose, hydroxymethyl cellulose, hydroxyethyl cellulose, ethylhydroxyethyl cellulose, hydroxypropyl cellulose, ethyl cellulose, and benzyl cellulose; as well as cellulose esters such as cellulose acetate, cellulose butylate, cellulose acetate butylate, cellulose propionate, cellulose butyrate, cellulose acetate propionate, cellulose acetate butyrate, and cellulose acetate phthalate. The amount of the protecting colloid in the first solution is sufficient to reduce microdroplet coalescence in the aqueous/organic suspension, and is generally between about 0.1% and about 3% by weight % of the first solution. Preferred is methyl cellulose at about 0.5% to about 0.6% by weight.

An emulsifier is included in the first solution to promote the formation of a stable emulsion on addition of the first solution to an organic second solution (described below). Any emulsifier which stabilizes the aqueous/organic emulsion may be used. Suitable emulsifiers include, but are not limited to, alkylaryl polyether alcohols such as the Triton™ X nonionic surfactants commercially available from Union Carbide (Danbury, Conn.). These products generally contain mixtures of polyoxyethylene chain lengths and include, for example, Triton® X-100: polyoxyethylene(10) isooctylphenyl ether; Triton® X-100, reduced: polyoxyethylene(10) isooctylcyclohexyl ether; Triton® N-101, reduced: polyoxyethylene branched nonylcyclohexyl ether; Triton® X-114: (1,1,3,3-tetramethylbutyl)phenyl-polyethylene glycol; Triton® X-114, reduced: polyoxyethylene(8) isooctylcyclohexyl ether; Triton® X-405, reduced: polyoxyethylene(40) isooctylcyclohexyl ether; and Triton™ X-405: polyoxyethylene (40) isooctylphenyl ether, 70% solution in water. Particularly suitable is Triton™ X-405, 70 wt % solution, which is an alkylaryl polyether alcohol preparation having an average of at least about 30 ethylene oxide units per ether side chain. Typically, the emulsifier in the first solution is used at a concentration of about 1% to about 10% by weight % of the first solution.

In addition, the first solution includes a polymerization initiator. The initiator used in the process of the invention is a water soluble azo initiator which has a low temperature of activation. Azo initiators are substituted diazo compounds that thermally decompose to generate free radicals and nitrogen gas. The temperature of activation of the azo initiator used is low enough so that the boiling point of an organic second solution (described below) is above the azo initiator activation temperature. Examples of suitable low temperature water soluble azo initiators include, but are not limited to, 2,2'-azobis(2-amidinopropane)dihydrochloride; 4,4'-azobis(4-cyanopentanoic acid); and 2,2'-azobis(2-[2-imidazolin-2-yl]) propane dihydrochloride. A particular azo initiator, having a particular activation temperature, is used with an organic second solution composition (described below) at a temperature and with a reaction time period that is effective in initiating polymerization. Most effective is use of an azo initiator at a temperature that is close to its optimal activation temperature and which is also below the boiling temperature of the organic second solution. However, an azo initiator may be used at a temperature that is lower than its optimal activation temperature in order to stay below the boiling temperature of the organic second solution, but this will require a longer reaction time for polymerization. A particularly suitable azo initiator has an activation temperature that is less than about 53° C. and this azo initiator is used with an organic second solution having a boiling temperature of about 55° C. A particularly suitable azo initiator is VA-044™ (2,2'-azobis(2-[2-imidazolin-2-yl])propane dihydrochloride, commercially available from Wako Pure Chemical Industries, Ltd., Richmond, Va.) having an activation temperature of between 51° C. and 52° C.

The azo initiator has advantages over other initiators such as persulfates and hydroperoxides. The azo initiator is effective when used in very low amounts, in contrast to other initiators. The azo initiator is used at about 0.1% to 1.0% by weight % of monomer. Preferably about 0.5% azo initiator is used. The low level of azo initiator results in very low levels of initiator contamination in the polymerized hydrogel as compared to contamination resulting from use of other initiators. In addition, there is no metal contamination resulting from the azo initiator, while other initiators typically include metal catalysts that do leave metal contamination in the polymerized product. In addition, other typical initiators are sensitive to oxygen, and, therefore, solutions in contact with these initiators must be de-aerated. The remaining oxygen content of the de-aerated solutions is variable, leading to inconsistency in the microsphere forming process. With use of an azo initiator, no de-aeration is required, which reduces the complexity of solution preparation for use in the microsphere formation process and increases the consistency of microsphere preparation. In addition persulfate initiators generally give more inconsistent conversion and yields of microspheres than azo initiators.

Second Solution

An organic solution acts as a dispersion medium in the process of microsphere preparation, and is herein called the "second solution". The second solution comprises at least one substantially chlorinated hydrocarbon of less than 6 carbon units, excluding halogenated aromatic hydrocarbons. A substantially chlorinated hydrocarbon may be a hydrocarbon that is at least 50% chlorinated, as well as a fully chlorinated hydrocarbon. Particularly suitable is a chlorinated solvent that readily dissolves ethyl cellulose to a homogeneous solution, boils above at least about 50° C. and has a density able to support microsphere formation in aqueous/organic suspension. A particularly useful organic medium in the process of microsphere preparation is a mixture containing chloroform and methylene chloride. Methylene chloride alone does not have a high enough boiling temperature to allow the use of a low temperature aqueous azo initiator. Chloroform alone is not sufficient to support microsphere formation. The combination of chloroform and methylene chloride provides an organic solution which has a boiling temperature allowing use of a low temperature aqueous azo initiator and which supports microsphere formation in the aqueous/organic suspension. Chloroform and methylene chloride may be used in volume ratios between about 20:1 and about 1:20. More suitable is a chloroform and methylene chloride solution with a volume ratio between about 5:1 and 1:5. Particularly suitable is a volume ratio of 3:1 chloroform:methylene chloride solution which has a boiling temperature of about 53° C.

Additionally, other solvents or solvent mixtures may be used in combination with a substantially chlorinated hydrocarbon such as methylene chloride. For example, it may be desirable to substitute for chloroform in the chloroform-methylene chloride mixtures described above because of the health hazards of chloroform. Suitable solvent or solvent mixtures to substitute for chloroform may be selected by matching the Hansen solubility parameters (Hansen, *Hansen Solubility Parameters, A User's Handbook*, CRC Press LLC, Boca Raton, Fla., 2000) of particular solvent or solvent mixtures to those of chloroform. The Hansen solubility parameters are an extension of the Hildebrand solubility parameters. According to Hansen, "the basis for the Hansen Solubility Parameters (HSP) is that the total energy of vaporization of a liquid consists of several individual parts, that arrive from (atomic) dispersion forces, (molecular) permanent dipole-permanent dipole forces and (molecular) hydrogen bonding (electron exchange)." Materials having similar HSP have high affinity for each other. The basic equation for the HSP is that the total cohesion energy, E, must be the sum of the individual energies:

$$E = E_D + E_P + E_H$$

Where $E_D$ is the Hansen dispersion cohesion energy, $E_P$ is the Hansen polarity cohesion energy, and $E_H$ is the Hansen hydrogen bonding cohesion energy. Dividing this expression by the molar volume, gives the total Hildebrand solubility parameter as the sum of the squares of the Hansen components:

$$\delta^2 = \delta_D^2 + \delta_P^2 + \delta_H^2$$

Chloroform has a Hansen dispersion of 17.8, Hansen polarity of 3.1 and Hansen hydrogen bonding of 5.7 in units of the square root of megapascals ($mPa^{1/2}$). A software program (Molecular Modeling Pro Plus, ChemSW, Fairfield, Calif.) is available to calculate the Hansen solubility parameters from molecular structure. Preferred solvent mixtures have a sum of the differences (in absolute value) in Hansen solubility parameters relative to the Hansen solubility parameters of chloroform of less than about 0.21. A sample calculation of the sum of the differences in Hansen solubility parameters for a mixture of 30 vol % (percent by volume) ethyl heptanoate and 70 vol % phenethyl acetate relative to chloroform is shown in Table A. Suitable solvent mixtures are given in Table B.

TABLE A

Calculation of the Sum of the Differences in Hansen Solubility Parameters for a Mixture of 30 vol % Ethyl Heptanoate and 70 vol % Phenethyl Acetate relative to chloroform

| Hansen Parameter | [1] Chloroform | [2] Ethyl Heptanoate | [3] Penethyl Acetate | 0.3 × [2] + 0.7 × [3] | Difference |
|---|---|---|---|---|---|
| Dispersion | 17.8 | 16.254 | 18.520 | 17.840 | 0.040 |
| Polarity | 3.1 | 3.025 | 3.123 | 3.093 | 0.007 |
| Hydrogen Bonding | 5.7 | 4.686 | 6.034 | 5.630 | 0.070 |

Sum of differences = 0.117

TABLE B

Solvent Mixtures that Can be Substituted for Chloroform

| Solvent Mixture (% by volume) | Difference in Hansen Solubility Parameters Relative to Chloroform |
|---|---|
| 20% methyl oleate: 80% phenethyl acetate | 0.1180 |
| 30% ethyl heptanoate: 70% phenethyl acetate | 0.1170 |
| 30% methyl octanoate: 70% phenethyl acetate | 0.1352 |
| 40% diethyl carbonate: 60% methylphenyl acetate | 0.1457 |
| 20% phenylpropyl methyl ether: 80% phenyl propyl ether | 0.1501 |
| 70% ethyl phenyl ether: 30% phenylpropyl acetate | 0.1570 |
| 20% diethylene glycol butyl ether: 80% phenylpropyl methyl ether | 0.1703 |

TABLE B-continued

Solvent Mixtures that Can be Substituted for Chloroform

| Solvent Mixture (% by volume) | Difference in Hansen Solubility Parameters Relative to Chloroform |
|---|---|
| 20% ethyl propionate: 80% phenylpropyl acetate | 0.1740 |
| 80% phenylpropyl acetate: 20% tripropylamine | 0.1856 |
| 90% phenyl propyl ether: 10% toluene | 0.2015 |
| 30% methyl hexanoate: 70% phenylpropyl acetate | 0.2048 |
| 20% isopropyl palmitate: 80% phenethyl acetate | 0.2073 |

In one embodiment, the second solution comprises a combination of a solvent mixture of 30 vol % ethyl heptanoate (CAS No. 106-30-9) and 70 vol % phenethyl acetate (CAS No. 103-45-7), with methylene chloride in a volume ratio of about 20:1 to about 1:20, in addition about 5:1 to about 1:5, and further in addition of about 3:1.

The second solution also comprises a viscosity modifying component that provides a surface tension that allows droplet formation in the aqueous/organic suspension formed during the present microsphere preparation process. This viscosity modifying component is again called a "protecting colloid". A variety of natural and synthetic compounds soluble in organic media may be used as a protecting colloid, including, but not limited to, cellulose derivatives, polyacrylates (such as polyacrylic acid and polymethacrylic acid), polyalkylene glycols such as polyethylene glycol, partially hydrolyzed polyvinyl alcohol and other polyols, guar gum, and agar gum. Particularly useful are cellulose ethers such as methyl cellulose, hydroxymethyl cellulose, hydroxyethyl cellulose, ethylhydroxyethyl cellulose, hydroxypropyl cellulose, ethyl cellulose, and benzyl cellulose; as well as cellulose esters such as cellulose acetate, cellulose butylate, cellulose acetate butylate, cellulose propionate, cellulose butyrate, cellulose acetate propionate, cellulose acetate butyrate, and cellulose acetate phthalate. The amount of the protecting colloid in the organic second solution is sufficient to reduce microdroplet coalescence in the aqueous/organic suspension, and is generally between about 0.5% and about 5% by weight % of the organic second solution. Particularly suitable is ethyl cellulose at about 1.5% by weight.

Process for Microsphere Preparation

The first solution and the second solution are combined with agitation to form a first suspension. The second solution is used in an amount that is adequate to form a good suspension, while the amount may be as great as is practical. Generally the volume ratio of second to first solutions is in the range of about 10:1 to about 2:1. Preferably the volume ratio of second to first solutions is in the range of about 6:1 to about 4:1.

The first and second solutions may be combined in any order. Specifically, the first solution can be added to the second solution, the second solution can be added to the first solution, or the two solutions can be combined simultaneously. Preferably, the first solution is added to the second solution. During the combination of the first and second solutions, the resulting mixture is agitated at a rate capable of forming a uniform suspension from the two solutions. Agitation may be by any method which thoroughly mixes the two solutions, such as shaking or stirring. Typically, the second solution is stirred in a container while the first solution is poured into the same container. The combined first and second solution is agitated at a temperature that is below the azo initiation temperature (and above the freezing point of the solution) to form a uniform, first suspension. Generally the temperature is below about 50° C., and more typically is below about 40° C. A temperature that is below about 30° C. is preferred. Typically the first suspension is stirred at about 100 to 600 rpm, depending on the size of the container, at room temperature for about one-half to one hour.

The agitation of the first suspension allows formation of small droplets in the suspension. The size of the forming droplets, and therefore the size of the microspheres that are produced, is related to the rate of agitation. As the agitation is reduced, droplets coalesce. Agitation is maintained at a rate sufficient to reduce droplet coalescence allowing the formation of micron sized microspheres. For example, for the formation of microspheres in the size range of 40 to 500 microns, stirring is typically about 150-250 rpm when using a one liter container. The optimum agitation rate for any particular system will depend on many factors, including the particular monomer, crosslinking agent, and solvent system used, the geometry of the container, the geometry of the agitator, and the desired microsphere properties for the intended application. For example, the size of the microspheres depends on the agitation rate. In general, larger microspheres are obtained at lower agitation rates. The agitation rate for any given conditions can be readily optimized by one skilled in the art using routine experimentation.

After the formation of the first suspension, a low level of heat is applied such that the temperature of the first suspension is brought to a temperature that is below the boiling temperature of the first solution, and below or at the boiling temperature of the second solution. Typically the temperature is between about 50° C. and 55° C., depending on the mixture of the second solution. It is preferred to bring the temperature of the first suspension made with a chloroform and methylene chloride ratio of about 3:1 to about 51° C. to 52° C. At this temperature the low temperature azo initiator is activated. The first suspension is agitated until it forms a second suspension comprising a precipitate of gelatinous microspheres in the suspending medium, which is predominantly an organic liquid phase. The gelatinous precipitate appears as a milky material which falls out of the suspension. Additionally, a white foam may be seen on top of the second suspension. Typically stirring of the first suspension to form the second suspension at the elevated temperature is for about 8-10 hours. The second suspension is agitated for another period of time at room temperature to ensure that the polymerization and microsphere formation is complete. During this time the second suspension cools to a temperature which is easily handled. Generally this is at or below about 30° C. Room temperature, typically at about 25° C., is conveniently used. Typically stirring remains at about 150-250 rpm, when using a one liter container, for about 8-14 hours.

Agitation is ceased, allowing the formed microspheres to settle to the bottom of the container. Removing the water from these hydrogel microspheres may be accomplished by washing with a dehydrating solvent such as methanol, ethanol, or acetone. Particularly useful is methanol, which is added, and the mixture is optionally agitated gently for about an hour to allow good solvent exchange. The microspheres are then recovered by a method such as by decanting or filtering, and may be washed a second time with methanol and again recovered. With removal of the water, the microspheres change in appearance from milky and gelatinous to hard and opaque white. The microspheres finally may be washed in ethanol, which is desirable for removal of residual methanol, particularly for microsphere use in medical applications. The washed microspheres in ethanol form one type of microsphere slurry. The microspheres optionally may be dried to form a powder of microspheres. Drying rids the microspheres of remaining washing solvent and additional water. Drying may be by any standard method such as using air, heat, and/or vacuum. Particularly useful is drying under vacuum in a vacuum oven set at about 20° C. to about 100° C. with a nitrogen purge. The use of lower drying temperatures requires longer drying times. For preparation of highly swellable microspheres, drying at room temperature (i.e., about 20° C. to about 25° C.) under vacuum with a nitrogen purge is preferred (see Example 34). A small amount of water generally remains in the microspheres after drying. The amount of remaining water may be about 1% to 10% of the microsphere total weight. The resulting microsphere preparation, though retaining a small amount of water in the microspheres, flows when tilted or swirled in a container and thus forms a free-flowing microsphere powder.

Microsphere Physical Properties

Microspheres prepared according to the present process are substantially spherical. A population of microspheres has sphericity measurements centered near about 95%, within a range of about 80% to about 100%. The population may include some individual microspheres which have a lower sphericity measurement, while maintaining the high sphericity measurement for the population as a whole.

The microspheres are in the size range of about 10 to about 730 microns in diameter, in addition from about 14 to about 730 microns in diameter. A prevalence of the microspheres are in the size range of about 25 to about 250 microns in diameter, as seen when analyzing a small sample size of microspheres. A heterogeneous size mixture of microspheres may be separated into microsphere samples of specific size ranges, if desired, for specific applications. Microspheres may be separated by methods such as fluidized bed separation and sieving, also called screen filtering. Particularly useful is sieving through a series of sieves appropriate for recovering samples containing microspheres of desired sizes. For example, separate samples of microspheres may be obtained using a series of sieves with mesh sizes of 35 to 400 microns. Separate microsphere samples may be obtained that have diameters ranging between about 30 and about 44 microns; about 115 and about 165 microns; about 180 and about 330 microns; and with size ranges also falling between and outside of these exemplary groups. These samples of size separated microspheres exemplify the production of microsphere preparations having a predominant size ranging between about 30 microns and 600 microns in diameter and including microspheres in a size range that is generally within +/−30% of the median for about 90% of the sample. Microsphere preparations may be produced having microspheres in a size range that is generally within +/−20% of the median for about 90% of the sample.

The microspheres prepared according to the present process have a high density, yet a high capacity for swell. The microspheres have low porosity, especially as compared to the microspheres described in U.S. Pat. No. 6,218,440, as viewed by scanning electron microscopy (SEM). The microspheres of U.S. Pat. No. 6,218,440 have cavities joined by interconnecting pores wherein at least some of the cavities at the interior of the material communicate with the surface of the material. These microspheres have pores throughout and a rough porous surface as well. The microspheres prepared by the present process have by comparison a relatively small number of voids embedded within a solid material. Generally, although not invariably, these voids are closed cell voids that are not interconnected to each other or to the surface of the microsphere. The surface of the present microspheres is generally smooth and rounded, although some surface imperfections may be present. The porosity of microspheres can also be assessed by density measurements. One preparation of microspheres prepared by the present process had a bulk density of 0.68 g/cm$^3$ (Example 6). It is expected that microspheres produced by the present process will have a bulk density of at least about 0.5 g/cm$^3$. In contrast, the bulk density of microspheres prepared according to one method in the prior art (U.S. Pat. No. 6,218,440 Example 2) was measured to be 0.182 g/cm$^3$ (see present Example 6). Individual microsphere density of the present microspheres is between about 0.9 g/cm$^3$ and about 2 g/cm$^3$, while the individual density of microspheres prepared according to one method in the prior art (U.S. Pat. No. 6,218,440 Example 2) was measured to be 0.8 g/cm$^3$ or less (see present Example 6).

The density, and porosity, of microspheres play a role in the durability of the microspheres. The microspheres prepared by the present process are highly durable in that the swelled microspheres have substantial resistance to fracture as they are passed through a small bore needle. Under the same conditions, swelled highly porous microspheres do fracture, and thus have low durability. For example, microspheres prepared by the present process that are swelled and passed through a 20 gauge needle maintain an average diameter similar to that of the starting sample, while the average diameter of microspheres prepared according to one method in the prior art (U.S. Pat. No. 6,218,440 Example 2) after passing through a 20 gauge needle is reduced by almost half indicating fracture of the particles.

As described above, the swell capacity (amount of water uptake) of microspheres prepared by the present process may vary depending on the amount of crosslinking agent added to the first solution. For example, crosslinking agent may be added in such an amount as to impart a swell capacity to the microspheres of about 50 grams of water per gram of microspheres, an amount to impart a swell capacity of about 70 grams per gram of microspheres, and alternatively an amount to impart a swell capacity of about 100 grams per gram of microspheres. Particularly suitable is a microsphere preparation having at least 70 grams of water uptake per gram of microsphere powder. Using the same amount of crosslinking agent, microspheres prepared according to one method in the prior art (U.S. Pat. No. 6,218,440 Example 2) had less than half of this swell capacity (see Example 6, Table 7).

The microspheres made by the present process exhibit rapid swell. Individual microspheres can be seen to reach a maximum size within about 15 sec of contacting the microspheres with water. Thus the individual microspheres reach their full swell capacity within about 15 sec, and typically within about 10 sec. A population of microspheres also has rapid swell as long as each microsphere has sufficient exposure to water. In general, when contacting a population of microspheres with water, those microspheres in the center of the population, or on the bottom of a container, do not have full exposure to water so that their swell time is longer. For example 1 gram of microspheres may reach 50% of full swell in 5 sec and about 70% of full swell in 10 sec with water exposure as described in the General Methods. Generally full swell is reached within 30 sec for a population of microspheres under the described water contact conditions.

An additional attribute of the microspheres prepared by the present process is the capacity to deform following swell. When placed under pressure, the swelled microspheres do not maintain their substantially spherical shape, but compress in the axis of the pressure and expand in the axis that is perpendicular to the pressure. Thus environmental factors, such as pressure of a flowing medium or from the walls of an enclosing container, may cause deformation of the microspheres. In addition, pressure of individual microspheres next to each other may cause deformation. This ability to deform is thought to be imparted and enhanced through the closed cell void structure of the microspheres. While not wishing to be bound by theory, it is thought that the closed cell voids are able to compress allowing the swelled hydrogel in the microspheres to deform maximally.

This ability to deform allows the microspheres to take on a shape of a containing space, and to fill that space. Additionally, deformed microspheres have increased surface area contact with each other, as compared to the contact area between spherical beads. The increased surface area contact between the deformed microspheres provides a more compact structure than is achievable with non-deforming spherical microspheres. This compact structure provides high resistance to penetration. The deformability is highly desirable in some applications such as in embolization treatment, where the deformed, compact microspheres may provide strong blockage at target vascular sites. In a test system that uses a flexible, substantially nonexpendable tubing having an internal diameter of 1.58 mm, the swelled, deformed microspheres were able to form occlusions that withstood very high pressures. For example, 15 mg of dry microspheres, when fully swelled, formed microsphere occlusions that were not dislodged by water pressure less than about 114 mm Hg (15.2 kilopascals (kPa)). Starting with 18 mg of dry microspheres the occlusions formed were dislodged by water pressure at about 570 mm Hg (76.0 kPa), and starting with 20 mg of dry microspheres the occlusions formed withstood over 1,000 mm Hg of pressure (133 kPa).

Microsphere Properties Advantageous for Medical Applications

Microspheres prepared by the present process are biocompatible in that they lack cytotoxicity, are non-inflammatory, and are non-hemolytic. The microspheres have a swell response in whole blood that is similar to the swell response in water, achieving up to 100-fold swell within seconds. These properties allow the microspheres described herein to be used in medical applications, where advantage may be taken of their full swell potential. In addition, the resistance to fracture of the microspheres described herein makes them particularly suitable for embolization since resistance to fracture reduces the potential for effects such as embolism downstream of the target site, unwanted inflammatory response, exacerbation of clotting cascade, and loss of therapeutic occlusion.

The Microsphere Preparation

The microsphere preparation of the present invention is prepared according to the present process and contains swellable/deformable microspheres having the properties described herein. The microsphere preparation may be the direct product of the process prior to drying, where the microspheres form a microsphere slurry including extraction solvent. The additional drying step of the process produces a microsphere powder. The microsphere powder may be made available for use as a powder or for addition of a liquid appropriate to the intended use. Addition of a liquid to the microsphere powder produces a microsphere slurry or microsphere suspension. Liquids used in a microsphere suspension may be any that are appropriate for the intended use. For example, a biocompatible liquid that controls swell is used to suspend microspheres for medical uses, such as tissue augmentation, wound treatment, and embolization. Typical swell-control biocompatible liquids include, for example, propylene glycol, dimethylsulfoxide (DMSO), Ethiodol®, MD-76®, and mineral oil. Ethiodol® and MD-76® are contrast agents typically used in medical intravascular arteriography or lymphography procedures. Ethiodol® contains iodine organically combined with ethyl esters of the fatty acids of poppyseed oil and is available from SAVAGE Laboratories® (Melville, N.Y.). MD-76® is an aqueous solution of diatrizoate meglumine (CAS No. 131-49-7, 66 wt %) and diatrizoate sodium (CAS No. 737-31-5, 10 wt %) buffered with monobasic sodium, with a pH of 6.5 to 7.7, having organically bound iodide to provide for radiological visualization. MD-76® is manufactured by Mallinckrodt Inc. (St. Louis, Mo.).

Embolization Suspension

A microsphere preparation made according to the present process is used to prepare a suspension for embolization treatment, herein called an "embolization suspension". Sterility is an important factor in embolization treatment. The described microsphere preparation process including a final ethanol wash, provides a sterilization treatment. Further sterilization may be performed by extending the ethanol wash for a long period of time, such as overnight. Sterility may be enhanced by using additional measures such as carrying out the process for making the microspheres in a sterile environment, and treating the microsphere preparation with UV light, ethylene oxide or gamma radiation, as is known to one skilled in the art.

The embolization suspension includes a biocompatible carrier. The carrier provides not only a medium to suspend and administer the microspheres, but also to control the swelling of the microspheres. Typically, the carrier used in the suspension has a low enough viscosity to allow delivery of the microspheres through small-bore needles and catheters, such as those of 20 gauge or 7 French (F) or smaller. A gauge measurement is used for needles, while a French measurement is used for catheters, both of which designate the outside diameter. The inside diameter of a needle or catheter is related to the outside diameter, but also depends on the thickness of the wall and so can vary between manufacturers. Thus precise measurements of the inside diameters of needles and catheters are not specified by the gauge or French unit. However, inside bore diameters of specific catheters and needles are known or can readily be obtained by one skilled in the art. Biocompatible carriers that limit swell of the microspheres, and thus are swell-control media, include the commonly used contrast agents Ethiodol® (SAVAGE Laboratories®, Melville, N.Y.) and MD-76® (Mallinckrodt Inc., St. Louis, Mo.). In addition, swell may be controlled by salt concentration and ionic strength, as well as with pH or DMSO. Particularly suitable biocompatible carriers are those containing DMSO above about 60% concentration, those with an acidic pH, and contrast agents. The contrast agent MD-76® allows some swell, ranging between about 3.5× and about 7.5× the original volume, and may be used as a swell-control medium. Different carriers may be mixed, such as combining a percentage of DMSO and a contrast agent to establish the desired amount of microsphere swell (explained below) in the embolization suspension.

The microsphere concentration in the embolization suspension varies depending on the carrier used and the size catheter to be used for administering the suspension, which in turn depends on the size of the vasculature to be embolized. In addition, the size of the microspheres affects the concentration used, where samples of different sized microspheres may be prepared, for example by sieving, as described herein. For example, 250 mg/mL concentration of approximately 250 micron microspheres in DMSO (no swell) may be used with catheters of 6 F and larger. For delivery of high concentrations of microspheres with smaller catheters, such as 5 F and smaller, it may be desirable to have limited swell of the microspheres for administering the microsphere suspension. The limited swell may take place prior to or during the administering. The limited swell may be up to about 10× the original volume of the microspheres. Limited swell provides deformability of the microspheres which allows them to pass through small diameter catheters and needles. Limited swell may be achieved by methods such as adjusting the salt concentration, pH or DMSO concentration of the carrier, or with use of a contrast agent. For example, with about 50% or less DMSO concentration in the carrier, the microspheres begin to swell. In addition, the microspheres may swell to between about 3.5× and 7.5× the original volume in contrast agent. Passage through 5 F catheters may be achieved with suspensions containing, for example, 150 mg/mL of 250 micron microspheres in MD-76®. Also, embolizing suspensions containing 300 mg/mL of 50-150 micron microspheres in MD-76® can pass through a 5 F catheter. The specific size and concentration of microspheres, as well as the desired carrier, may be chosen by one skilled in the art for the particular embolization treatment to be performed.

Embolization Treatment

The embolization suspension containing the microsphere preparation made as described herein is administered to a mammal for embolization, as is known to one skilled in the art, for example as described in "Uterine Artery Embolization and Gynecologic Embolotherapy", Spies and Pelage, 2005 ISBN: 0-7817-4532-2 and in "Vascular and Interventional Radiology: Principles and Practice", Bakal et al., 2002 ISBN: 0-86577-678-4. Administration of the embolization suspension containing microspheres prepared by the present process is generally by passage through a catheter or needle into the vasculature of the mammal such that the microspheres reach a target site. As the embolization suspension contacts the blood in the vasculature, the swellable/deformable microspheres swell and form an occlusion. The occlusion effectively blocks the blood flow distal to the occlusion site. The occlusion site may be any target site where, for medical treatment, it is desired to block the flow of blood. For example, the occlusion site may be in a blood vessel that feeds a tumor such as a uterine fibroid or a cancerous tumor, in an arteriovenous malformation, or in a blood vessel where the blood is not contained, such as in the case of a stomach ulcer or injury. Preoperative embolization may also be performed to stop blood flow to a region targeted for surgery.

The swellable/deformable microspheres, made by the present process, surprisingly were found to provide more readily administered and more durable occlusion than expected and as previously described in the art. The functional embolic load, which is defined as the amount of dry microsphere mass required to establish an occlusion when reconstituted in blood substitute in a fixed diameter tubing, is lower than expected. Thus smaller catheters than expected may be used to deliver an effective functional embolic load of the swellable/deformable microspheres, as compared to treatment with microspheres known in the art. The delivery of swellable/deformable microspheres in small catheters, such as 5 F and 3 F catheters, allows better placement of microspheres by using the smaller catheters to more closely reach a target site. Use of smaller catheters also reduces the risk of vasospasm, caused by catheter irritation, which can result in abortion of the procedure or spurious end-point occlusions that disintegrate after vasospasm resolution. The use of small catheters is also enabled by the deformability of the microspheres, as described herein. Also due to their deformability the microspheres are capable of deep vessel penetration prior to occlusion, as seen in the porcine renal vasculature embolization in the Examples, below. The deep penetration also leads to enhanced packing of microspheres within the vessels, leading to robust occlusions.

The microspheres prepared as described herein form more durable occlusions than expected. This feature is most likely attributable to the swellable and deformable properties of the microspheres. The swelling of the microspheres within the elastic environment of the target artery creates a recoil force from the arterial wall which in turn deforms the microspheres, thereby creating a packed occlusion with maximal surface contact between deformed, swelled microspheres. The tight packing of the swelled, deformed microspheres was shown with in vivo studies of embolization in porcine renal vasculature. In addition, dislodging pressures were measured for swelled, deformed microsphere occlusions in vitro. The in vitro system used a 1.58 mm internal diameter tubing, which is of larger diameter than typical of target vessels and therefore more difficult to block. The tubing used for measuring the occlusion durability was flexible, and non-expandable at the test pressures used. Tubing such as Tygon® tube, specifically Beverage tubing (B-44-3) with an internal diameter of 1.58 mm, outer diameter of 4.76 mm and tubing wall thickness of 1.59 mm, is particularly suitable for the assay. Occlusions of microspheres prepared according to the process of the invention withstand physiological blood pressures, and much higher pressures. For example, 15 mg (measured dry mass) of microspheres of size 250-500 micron diameter form occlusions that withstand about 125 mm Hg (16.7 kPa), 18 mg of microspheres of size 250-500 micron diameter form occlusions that withstand about 600 mm Hg (80.0 kPa), and 20 mg of size 250-500 micron diameter microspheres form occlusions that withstand over 1,000 mm of Hg (133 kPa) in pressure.

The amounts of microspheres, prepared by the present process, that are capable of forming durable occlusions can easily be delivered through microcatheters. Suspensions of up to about 10 mg/mL of unswelled microspheres may be delivered through a 5 F catheter. Thus, less than 2 mL of a 10 mg/mL suspension of the present microspheres can form a durable occlusion as described above. The microspheres in a DMSO medium were also able to pass through a 3 F microcatheter when at a concentration of 10 mg/mL and 30 mg/mL.

Some typically used media, such as Ethiodol®, are too viscous to pass through microcatheters. Thus alternative media with low viscosity, yet the ability to limit microsphere swell, are used in embolization suspensions delivered with microcatheters. The small volume of microspheres, prepared by the present process, that is delivered for forming an occlusion allows the use of suspension media that may cause ill effects when injected into a mammal in larger volumes. For example, media including more than 60% DMSO or media with a pH in the range of 2-3 may be used in embolization suspensions to control microsphere swelling. Several milliliters of these media may be administered to deliver an adequate amount of microspheres to form an occlusion. Additionally, for minimizing effects of potentially harmful media, a buffering solution may be administered prior to and after administering the embolization suspension. Phosphate buffered saline or bicarbonate buffer are examples of solutions that may be used in this manner.

In addition to forming an occlusion, the present microspheres used in embolization may also be prepared such they are able to deliver medications, such as pharmaceutical drugs or therapeutic agents. The medication may be loaded into the microspheres using various methods known in the art. For example, the microspheres may be imbibed with the medication by swelling the microspheres in a medium containing the medication and allowing it to soak into the microspheres. The microspheres may then be dried or deswelled by removing water by washing with a dehydrating solvent, as described above. Additionally, the medication may be coated onto the microspheres using methods such as spraying, immersion, and the like. The medication may also be directly incorporated into the microspheres during their preparation by adding the medication to the first solution. Following delivery of the microspheres containing the medication to the target site, the pharmaceutical drug or therapeutic agent is released over time as the microspheres are in contact with body fluids. For example, anti-cancer drugs may be delivered by microspheres forming an occlusion in proximity to a cancerous tumor. Delivery in embolizing microspheres of agents such as anti-angiogenic factors, anti-inflammatory drugs, analgesics, and local anesthetics provide additional treatment to the physical blockage of embolization. Additional therapeutic agents that may be delivered in the present microspheres are described in WO 01/72281, which is herein incorporated by reference.

Kits

Further provided is a kit including swellable/deformable microspheres prepared according to the process described herein, which may be in a slurry, a powder, or a suspension. The quantity of microspheres in the kit may vary depending on the specific intended application. For example, as described above, an occlusion may be formed by different quantities of the present microspheres such as 15 mg, 18 mg, or 20 mg. The quantity of microspheres will depend on factors such as the diameter of the site to be occluded and the pressure that the occlusion must withstand. Particularly useful is a kit containing swellable/deformable microspheres, prepared according to the process described herein, in a suspension and optionally a syringe and/or a catheter for use in administering the microspheres. The kit may also include a biocompatible carrier. Typically included in a kit are instructions for use of the components.

EXAMPLES

The present invention is further defined in the following Examples. These Examples are given by way of illustration only, and should not be construed as limiting. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "sec" means second(s), "µL" means microliter(s), "mL" means milliliter(s), "L" means liter(s), "nm" means nanometer(s), "mm" means millimeter(s), "cm" means centimeter(s), "cm³" means cubic centimeters, "µm" means micrometer(s) or micron(s), "mM" means millimolar, "M" means molar, "g" means gram(s), "mol" means mole(s), "rpm" means revolutions per minute, "wt %" means percent by weight, "cP" means centipoise, "kGy" is kiloGray(s), "F" means French, "G" means gauge. In the designation $d^{20}_4$, d is density, the 4 is the temperature of the standard used to compare the densities, typically water at 4° C., and the 20 is the temperature at which the density of the subject material is measured.

General Materials and Methods

Chemicals and other ingredients were purchased from Aldrich (Milwaukee, Wis.) and used as received, unless otherwise specified. Solvents were purchased from EMD Chemical (Darmstadt, Germany) or Aldrich, as specified below. The VA-044 polymerization initiator was used as received from Wako Pure Chemical Industries, Ltd (Richmond, Va.). All cell culture media were purchased from American Type Culture Collection (ATCC, Manassas, Va.).

Method of Measurement of Microsphere Swell

Swell ratio was determined according to a method described in the following reference: Figuly, Garret D., et. al. *Macromolecules* 1997, 30, 6174-6184. Into a pre-dried, tared, 150 mL coarse fritted funnel was added approximately 1 g of microspheres. The stem of the funnel was sealed with a rubber stopper. The funnel was placed on a filter flask, and about 150 mL of distilled water at room temperature was added to the funnel and its contents. The contents were stirred, if necessary, to fully disperse the water and microspheres. The contents were left undisturbed for 15 min. The stopper was then removed from the stem of the funnel, and suction was applied for 5 min. The stem and the underside of the funnel were then rinsed with ethanol to remove any remaining water droplets, and suction was then continued for an additional 5 min. Any remaining water droplets were wiped off of the funnel. The funnel and contents were then weighed to determine the weight of water retained by the microspheres. Swell was calculated as follows:

$$\begin{aligned} \text{swell} &= [(\text{total mass of wet microspheres} + \text{funnel}) - \\ &\quad (\text{total mass of dry microspheres} + \text{funnel})]/ \\ &\quad \text{mass of dry microspheres} \\ &= [\text{wet mass of microspheres} - \text{dry mass of microspheres}]/ \\ &\quad \text{dry mass of micropheres} \\ &= \text{mass water retained (g)/mass of dry microspheres (g)} \end{aligned}$$

Example 1

Preparation of Swellable Microspheres Using Acrylic Acid and Microsphere Properties In a 5 L round-bottom, three-necked flask equipped with an overhead stirrer, thermometer, reflux condenser, and nitrogen inlet port was prepared a solution of 36.0 g ethyl cellulose, 1200 mL of chloroform, and 570 g of methylene chloride (solution A). The mixture was stirred at 100 rpm until the ethyl cellulose dissolved; then the agitator was increased in speed to 180 rpm to create a slight vortex. In a second flask, was prepared a solution of 1.50 g methyl cellulose, 3.00 g N,N'-methylenebisacrylamide (2.3 Mol % of monomer), 26.01 g Triton™ X-405 (polyoxyethylene (40) isooctylphenyl ether—70% solution in water), and 149.4 g water (solution B). In a third separate flask was mixed 58.5 g of acrylic acid and 81 g of a 25% aqueous sodium hydroxide solution (to reach a pH between 5 and 6) (solution C). This acrylic acid solution was then added to the water solution B.

At this point, while rapidly stirring the mix of Solutions B and C, 0.15 g of the water-soluble azo initiator VA-044 (2,2'-azobis(2-[2-imidazolin-2-yl])propane dihydrochloride) was added, and the resulting solution was stirred for 5 min. This solution (the "first solution") was then added to the round-bottom flask containing solution A (the "second solution"). The resulting reaction mixture was allowed to stir (the "first suspension") at 180 rpm for about 1 h at room temperature. The first suspension was then heated to 51° C. and stirred at 180 rpm for an additional 10 h at that temperature to allow substantial microsphere formation (the "second suspension"). The second suspension was then stirred at 180 rpm for another 14 h at room temperature to ensure complete polymerization. After this time, approximately 1200 mL of methanol was slowly added to the second suspension to remove water from the microspheres, and the microspheres were allowed to stir an additional hour. The microspheres were then filtered and washed with an additional 250 mL of methanol. They were filtered again and finally washed with 250 mL of ethanol. They were then dried in a nitrogen purged vacuum oven set at 100° C. The resulting microspheres were white in color. The final yield of dried microspheres was 73.4 g.

The resulting dried microspheres exhibited diameters generally ranging from 25 microns to 250 microns as measured from photos acquired via scanning electron microscopy. Microsphere swell was tested as described in General Methods. When exposed to water, the microspheres absorbed 89 g of water/g of microspheres.

Figure 1B:
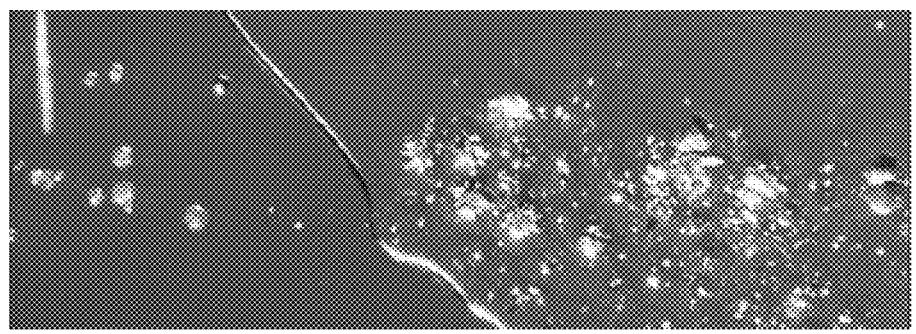
Figure 1C:
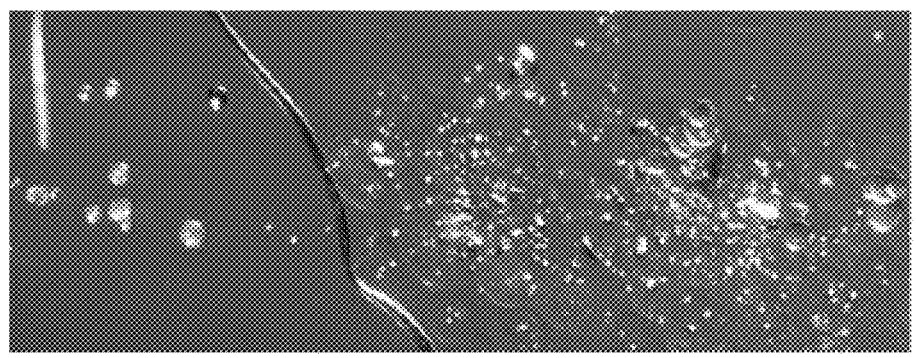

The microspheres were placed on a glass slide that was then placed under a microscope lens. A drop of water was placed on the slide. Movement of the water front across the slide was observed via a high speed multiple exposure digital camera, taking pictures at 2 frames per second. The images were recorded, as well as the time it took for the water front to move across the slide. The microspheres reached nearly maximal size in 4 sec. After 14 sec only a slight increase in microsphere size was observed. Images of the microspheres are shown in FIG. 1, with no water added in A), 4 sec after water contact in B), and 14 sec after water contact in C). Thus the microspheres showed very rapid swell, within a matter of seconds.

Figure 2A:
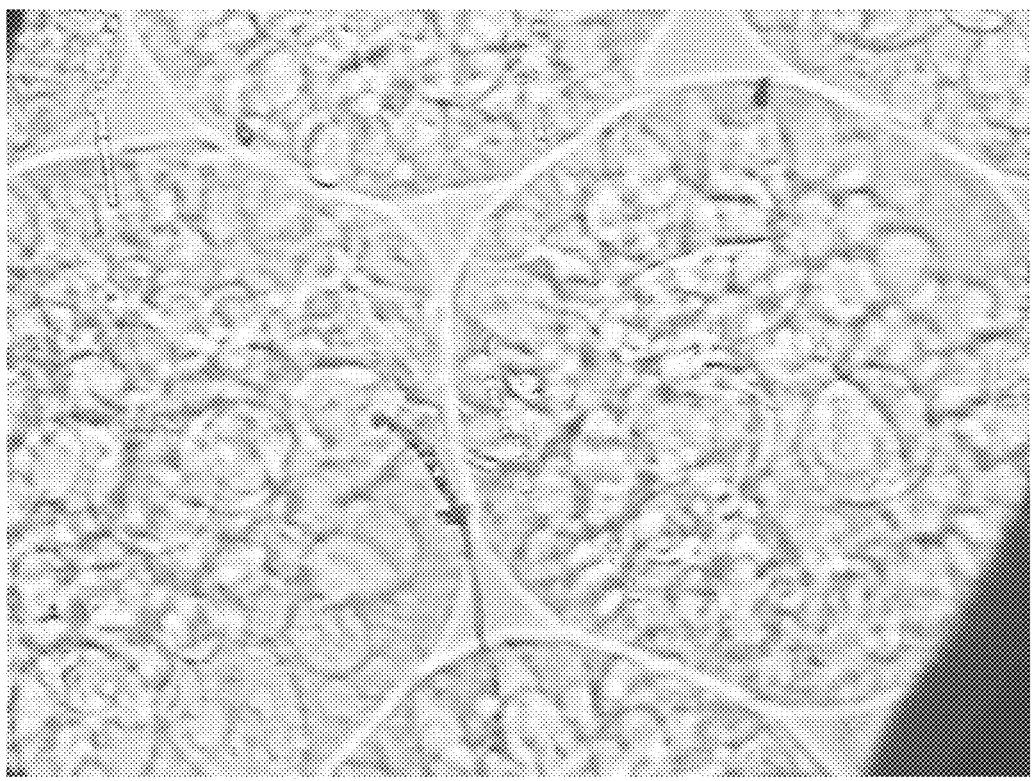
FIG. 2 shows in A) light microscopy showing deformation of contacting swelled microspheres, B) Scanning Electron Microscopy (SEM) showing the substantially smooth surface and substantial sphericity of microspheres prepared by the present process (without swell).

Swelled microspheres were observed under a light microscope. It was observed that microspheres in close contact with each other did not remain spherical, but instead showed deformation of the boundary surfaces thereby increasing the contact area between adjacent microspheres. The extent of the contacts between the swelled and deformed microspheres nearly eliminated open spaces between microspheres, as seen in FIG. 2A.

Figure 2B:
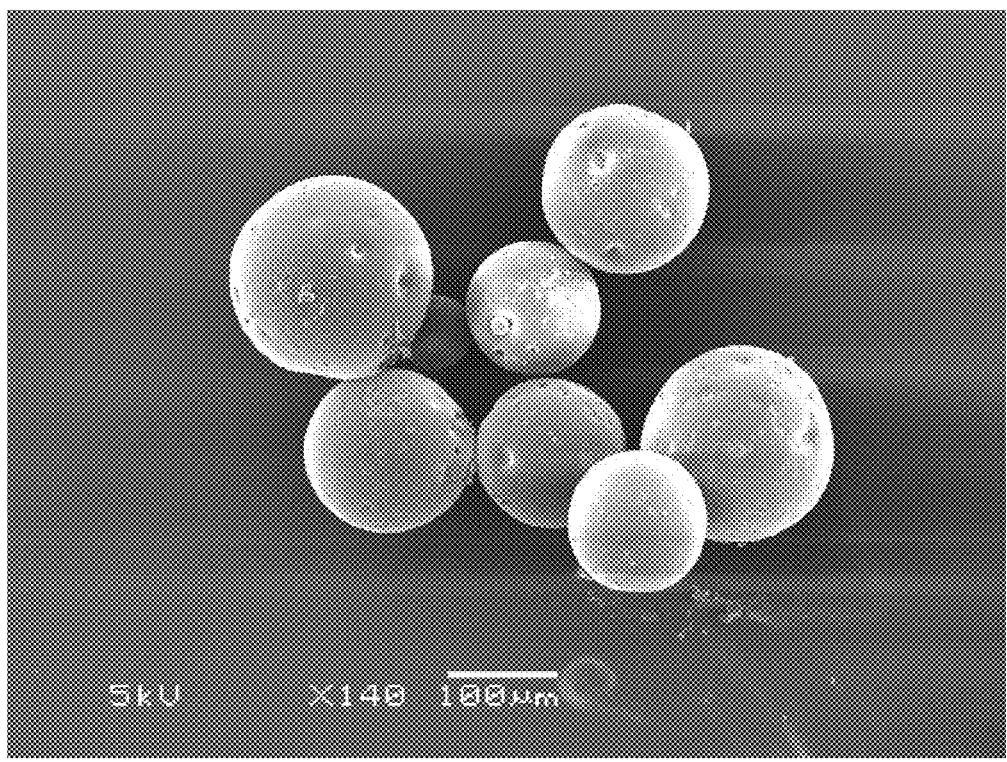

Sphericity measurements of microspheres were made on a bulk scale using the Beckman-Coulter™ RapidVUE® particle analysis system (Hialieahgg, Fla.), using an adaptive threshold value of 56%. A 20 mg sample of microspheres was suspended in 75 mL of water (swelled microspheres), a 50 mg sample of microspheres was suspended in 75 mL of DMSO (unswelled microspheres), and both samples were assayed in the particle analyzer. The results showed that both swelled and unswelled microspheres were close to spherical with a measured sphericity centered near 95%, indicating a high degree of sphericity for the microspheres prepared by the process described in this Example. A picture of unswelled microspheres is shown in FIG. 2B.

Example 2

Control of Swellable Microspheres Water Uptake via Crosslink Density

All of the samples for this study were prepared in the following manner, where the only ingredient that was varied was the amount of the crosslinking agent N,N'-methylenebisacrylamide. Values for this ingredient are displayed in Table 1 as both gram quantity of crosslinking agent, and Mol % of crosslinking agent with respect to the sum of the moles of monomer+crosslinking agent in the reaction mixture.

In a 1 L round-bottom, three-necked flask equipped with an overhead stirrer, thermometer, reflux condenser, and nitrogen inlet port was prepared a solution of 12.0 g ethyl cellulose, 400 mL of chloroform, and 190 g of methylene chloride (solution A). The mixture was stirred at 150 rpm until the ethyl cellulose dissolved; then the agitator was increased in speed to 250 rpm to create a slight vortex. In a second flask was prepared a solution of 0.50 g methylcellulose, varying amounts (see Table 1 below) of N,N'-methylenebisacrylamide, 8.67 g Triton™ X-405-70% solution, and 49.8 g water (solution B). In a third separate flask was mixed 19.5 g acrylic acid and 25 g of a 25% aqueous sodium hydroxide solution (to reach a pH of 5.3) (solution C). This acrylic acid solution was then added to the water solution B.

At this point, while rapidly stirring the mixture of solutions B and C, 0.05 g of the water soluble azo initiator VA-044 (2,2'-azobis(2-[2-imidazolin-2-yl])propane dihydrochloride) was added, and the resulting solution was stirred for 5 min. This solution (the "first solution") was then added to the round-bottom flask containing solution A (the "second solution"). The reaction mixture, which formed a suspension, was allowed to stir at 250 rpm for about 1 h at room temperature (the "first suspension"). The first suspension was then heated to 51° C. and stirred at 250 rpm for an additional 8.5 h at that temperature to allow substantial microsphere formation (the "second suspension"). The second suspension was then stirred at 250 rpm for another 14 h at room temperature to ensure complete polymerization. After this time, approximately 800 mL of methanol was slowly added to the second suspension, to remove water from the microspheres, and the microspheres were allowed to stir an additional hour. The microspheres were then filtered and washed with additional methanol. They were filtered again and finally washed with ethanol. They were then dried in a nitrogen purged vacuum oven set at 100° C. The resulting microspheres were white in color. The microsphere yield for each sample is given in Table 1.

Figure 3:
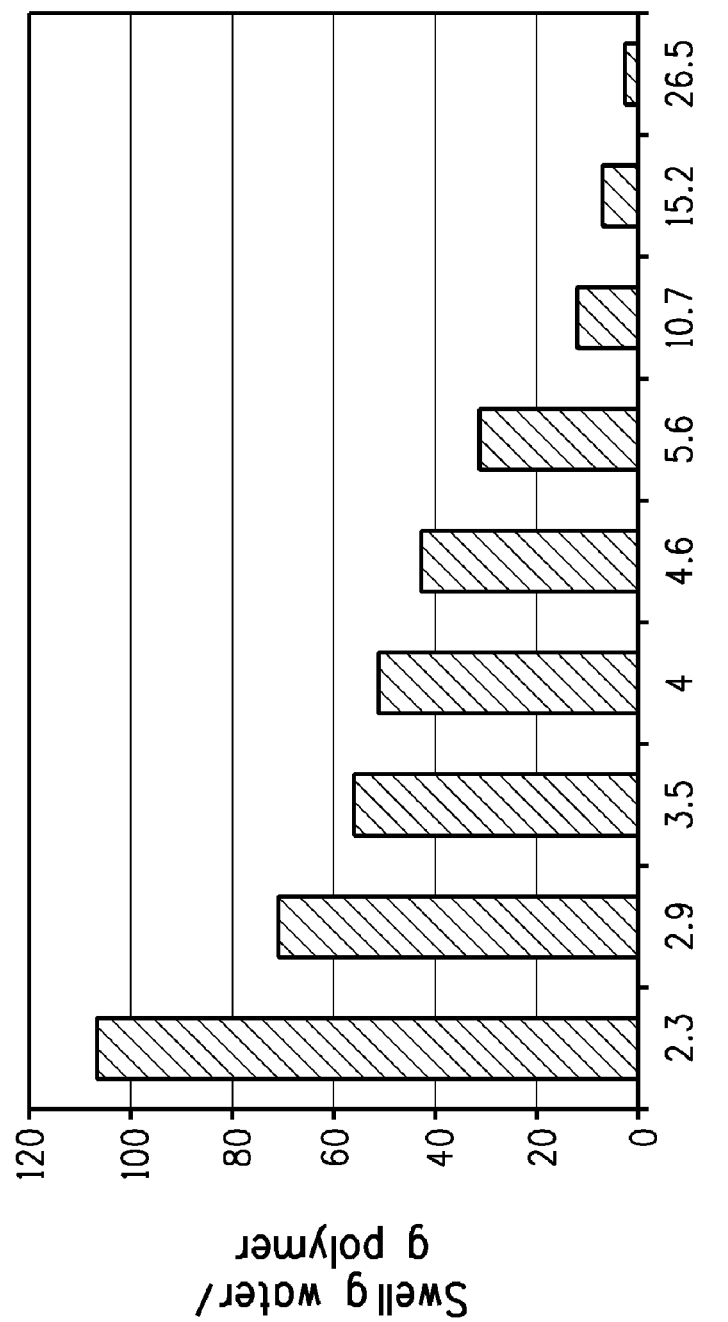
FIG. 3 shows a graph of microsphere swell capacity vs. amount of crosslinking agent.

Microsphere swell was tested as described in General Methods. Results of water uptake by each sample of microspheres having a different amount of crosslinking agent, also calculated as mole percent of crosslinker, are shown in Table 1 and a graph of this data is shown in FIG. 3.

TABLE 1

Effects of crosslinker on microsphere yield and swell

| Sample | crosslinker (g) | Mol % crosslinker | Swell (g H$_2$0/g microspheres) | yield (g) |
|---|---|---|---|---|
| 1 | 1.00 | 2.3 | 107.4 | 23.9 |
| 2 | 1.25 | 2.9 | 72.2 | 24.0 |
| 3 | 1.50 | 3.5 | 55.8 | 24.8 |
| 4 | 1.75 | 4.0 | 50.7 | 24.8 |
| 5 | 2.00 | 4.6 | 42.7 | 24.9 |
| 6 | 2.50 | 5.6 | 32.3 | 29.8 |
| 7 | 5.00 | 10.7 | 11.5 | 29.4 |
| 8 | 7.50 | 15.2 | 4.8 | 32.8 |
| 9 | 15.0 | 26.5 | 1.5 | 37.1 |

As can be observed from Table 1 and the graph in FIG. 3, as crosslinker content increased, the swell decreased. This result indicates that swell behavior of the microspheres can be tailored by adjusting the molar ratio of crosslinking agent to monomer in the ingredient mix of the microsphere preparation.

Example 3

Control of Swellable Microsphere Water Uptake via Initial pH of Acrylic Acid Monomer All of the samples for this study were prepared in the following manner, where the only ingredient that was varied was the amount of sodium hydroxide solution added to adjust the pH of the acrylic acid monomer. Values for this ingredient are displayed in Table 2.

In a 1 L round-bottom, three-necked flask equipped with an overhead stirrer, thermometer, reflux condenser, and nitrogen inlet port was prepared a solution of 12.0 g ethyl cellulose, 400 mL chloroform, and 190 g methylene chloride (solution A). The mixture was stirred at 150 rpm until the ethyl cellulose dissolved; then the agitator was increased in speed to 250 rpm to create a slight vortex. In a second flask, was prepared a solution of 0.50 g methyl cellulose, 1.00 g N,N'-methylenebisacrylamide (2.3 Mol %), 8.67 g Triton™ X-405 (70% solution), and 49.8 g water (solution B). In a third separate flask was mixed 19.5 g acrylic acid and varying amounts (see Table 2) of a 25% aqueous sodium hydroxide solution (solution C). The total volume of solution C was made constant for each sample by addition of water. The pH of each sample acrylic acid solution C was measured (Table 2). This acrylic acid solution was then added to the water solution B.

At this point, while rapidly stirring the mixture of Solutions B and C, 0.05 g of the water soluble azo initiator VA-044 (2,2'-azobis(2-[2-imidazolin-2-yl])propane dihydrochloride) was added, and the resulting solution was stirred for 5 min. This solution (the "first solution") was then added to the round-bottom flask containing solution A (the "second solution"). The reaction mixture was allowed to stir at 250 rpm for about 1 h at room temperature, forming the "first suspension". The first suspension was then heated to 51° C., and stirred at 250 rpm for an additional 8.5 h at that temperature to allow substantial microsphere formation (the "second suspension"). The second suspension was then stirred at 250 rpm for another 14 h at room temperature to ensure complete polymerization. After this time, approximately 800 mL of methanol was slowly added to the second suspension to remove water from the microspheres, and the microspheres were allowed to stir an additional hour. The microspheres were then filtered and washed with additional methanol. They were filtered again and finally washed with ethanol. They were then dried in a nitrogen purged vacuum oven set at 100° C. The resulting microspheres were white in color. The microsphere yield for each sample is given in Table 2.

The swell of microspheres prepared in each sample was tested as described in General Methods. Results of water uptake by each sample of microspheres having a different pH of solution C are shown in Table 2 and graphed in FIG. 4.

TABLE 2

Effects of pH on microsphere yield and swell

| Sample | 25% NaOH in water (g) | pH | Swell (g H$_2$0/g microspheres) | yield (g) |
|---|---|---|---|---|
| 1 | 0 | 1.85 | 0.7 | 20.1 |
| 2 | 1.8 | 2.80 | 6.1 | 19.8 |
| 3 | 5.1 | 3.45 | 131.3 | 19.2 |
| 4 | 15 | 4.35 | 88.5 | 21.4 |
| 5 | 30 | 5.31 | 107.4 | 23.9 |
| 6 | 41 | 6.41 | 84 | 25.9 |
| 7 | 42.69 | 7.28 | 83.5 | 25.8 |
| 8 | 42.8 | 8.35 | 126.5 | 15.7 |
| 9 | 42.84 | 9.82 | 130.3 | 18.2 |
| 10 | 42.86 | 10.13 | 115.4 | 18.2 |

Figure 4:
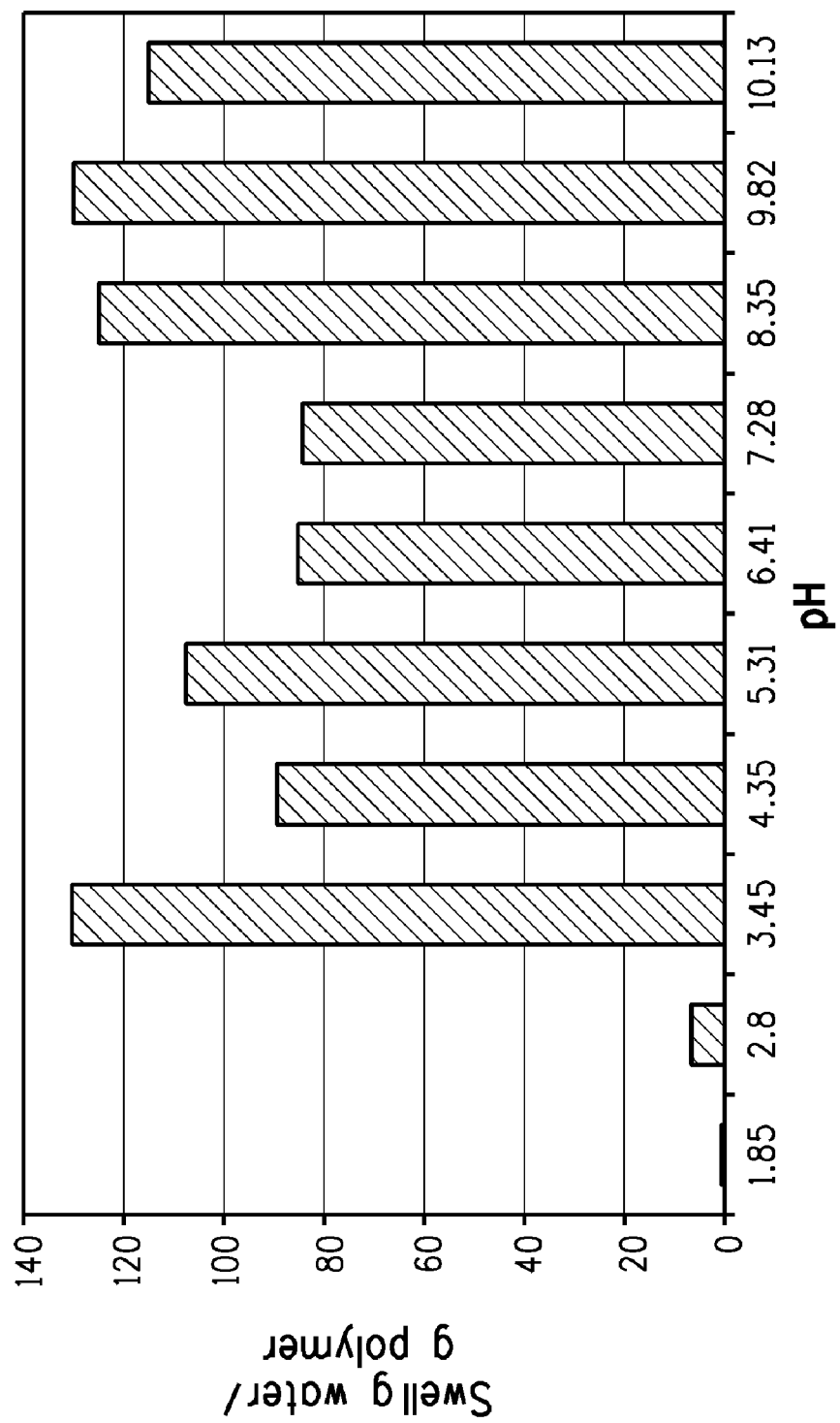
FIG. 4 shows a graph of microsphere swell capacity vs. pH of monomer solution.

As can be observed from the data in Table 2 and FIG. 4, non-neutralized acrylic acid, which produces a highly acidic polymer (low pH), produces microspheres with low swell capacity. However, once the monomer is neutralized to a pH of about 3.4, the resulting polymer becomes very hydrophilic, and high swells are produced. Further increasing the pH (neutralization of the acrylic acid) did not increase the ultimate swell capacity of the microspheres.

Example 4

Separation of Microspheres According to Size

A total of 15 batches of microspheres (1079 g) prepared according to Example 1 were combined and roll milled for 3 h to ensure good mixing. The microspheres were then passed through sieves as follows.

Eight-inch diameter sieves of desired sizes were stacked from the smallest opening at the bottom (nested into a pan) to the largest opening at the top. The sieve sizes used for separating the microspheres were:

| Microns | 500 | 250 | 180 | 125 | 75 | 38 | Pan |
|---|---|---|---|---|---|---|---|
| Mesh | 35 | 60 | 80 | 120 | 200 | 400 | — |

The entire sample was sieved (eliminating the need for riffling to obtain a representative sample). For this large sample, a small portion was sieved followed by another small portion. Aliquots were used that covered a sieve to a depth of about 32 mm to 48 mm. A cover was put on the top sieve and the stack of sieves was placed on a Gilson SS-5 Vibratory 3-In. Sieve Shaker. Each sample was run for 10 min with both the vibration and the tap activated.

The weights of seven containers were recorded and each was designated for a specific sieve fraction. Each sieve (or pan) was then dumped into its designated container. A Sigma-Aldrich Zerostat3 gun was used as needed to neutralize the static charge carried by the microspheres, and facilitate emptying each sieve. The sieves were restacked and the process repeated as many times as needed to process the entire sample. After the final portion was sieved, a brush was rubbed across the bottom of the sieve being dumped to dislodge near-sized particles wedged into the sieve openings. The net weight of each container was then determined and is given in Table 3. These results show that the predominance of microspheres ranged in size between 38 and 500 microns, with the 125 to 500 micron size being most prevalent.

TABLE 3

Size distribution of microspheres by sieving.

| Sieve Size | Microspheres Passing Through Sieve (g) |
|---|---|
| <38 microns | 1 |
| 38-75 microns | 13 |
| 75-125 microns | 74 |
| 125-180 microns | 138 |
| 180-250 microns | 443 |
| 250-500 microns | 377 |
| >500 microns | 1 |

The particle size for the sample recovered from each specific sieve was determined as follows. A Beckman Coulter Multisizer 3 was filled with a filtered 2:1 by volume methanol:glycerol mixture into which 3% (by weight) lithium chloride had been dissolved. An aperture tube was chosen which was suitable for the sieve fraction being measured. An aperture tube can detect particles with diameters falling in a range from 2 to 60% of the aperture diameter, and the largest particle dictates the size aperture. A 2000 micron aperture tube was used for the unsieved microspheres and for the >500 fraction. A 200 micron aperture tube was used for the 38-75 micron fraction and for the <38 micron fraction. For the intervening fractions a 1000-micron aperture tube was used. A round-bottomed beaker was filled with about 400 mL of the methanol/glycerol/lithium chloride electrolyte and placed on the sampling platform with the aperture tube immersed in the electrolyte.

Figure 5A:
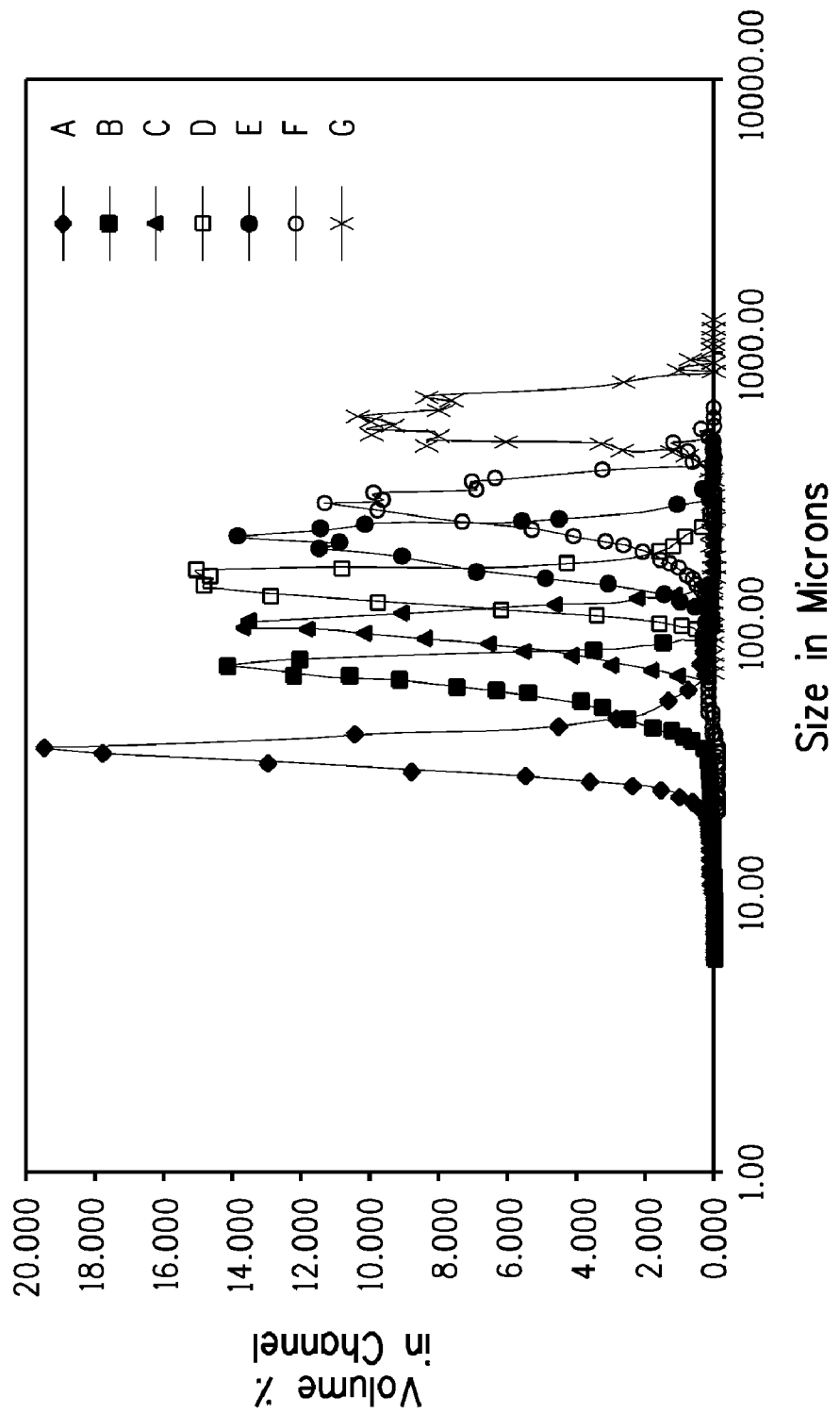
FIG. 5A shows a graph of the sizes of sieve-separated microsphere samples.
Figure 5B:
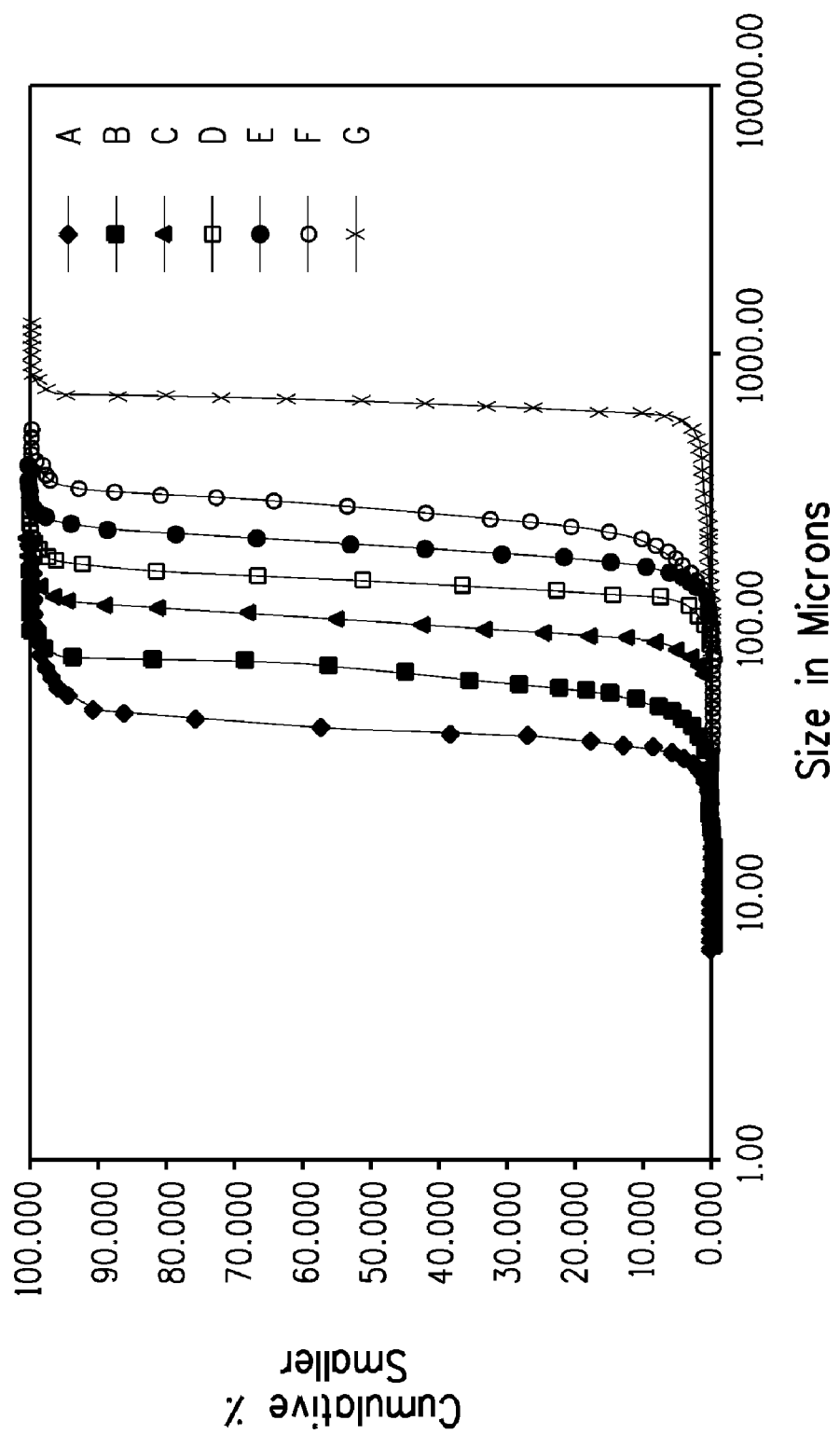
FIG. 5B shows a graph of the cumulative volume percent of sizes of sieve separated microsphere samples.

A spatula was used to stir and to extract from each sieve sample an aliquot of the microspheres to be measured that was added to a 20 mL cuvette containing methanol. The sample was placed in an ultrasonic bath for ten seconds. A medicine dropper was then used to transfer a portion of this slurry to a beaker sitting on the sampling platform. During the extraction the particles remained in motion so that a representative aliquot could be obtained. This was assured by using the medicine dropper as a stirrer, while at the same time continually drawing in and expelling the slurry. Either the entire content of the medicine dropper was used or, if only a portion was used, the dropper was rapidly moved from cuvette to the beaker and the portion to be used was spurted back into the beaker (this avoids size segregation caused by settling within the dropper). This transfer step was repeated as needed to bring the Multisizer's coincidence indicator to about 5%. The stirrer was then activated and set to a speed as high as possible without the risk of drawing air bubbles into the liquid. A manually controlled run was then begun, and stopped after 60 to 75 sec. The Multisizer data is shown in FIGS. 5A and 5B. As seen in FIG. 5A, the peak in microsphere size for each sieve sample is different from each other sample, with overlap in size at the boundaries. A graph of the cumulative microsphere size analysis is shown in FIG. 5B, and the resulting size distribution analysis is given in Table 4. Typically the peak for each sample shown in FIG. 5A is the 50% category.

TABLE 4

Cumulative Microsphere sizes in sieved microsphere samples
PARTICLE SIZE IN MICRONS AT CUMULATIVE VOLUME PERCENT FOR 7 MICROSPHERES BY BECKMAN COULTER MULTISIZER 3

| Sample; Sieve size | 10% | 25% | 50% | 75% | 90% |
|---|---|---|---|---|---|
| A; <38 microns | 29.97 | 33.97 | 37.24 | 39.94 | 44.18 |
| B; 38-75 microns | 14.06 | 56.33 | 66.08 | 73.65 | 78.30 |
| C; 75-125 microns | 77.88 | 89.06 | 101.50 | 112.00 | 120.50 |
| D; 125-180 microns | 116.90 | 127.80 | 140.30 | 153.10 | 163.00 |
| E; 180-250 microns | 149.90 | 168.20 | 189.70 | 210.20 | 227.80 |
| F; 250-500 microns | 182.10 | 224.10 | 258.10 | 294.90 | 330.10 |
| G; >500 microns | 438.30 | 497.20 | 576.20 | 659.00 | 729.90 |

Thus the microspheres may be separated into specific sized samples, each containing a predominant size of microsphere, with some variation in size. The size variation is within +/−30% of the median for 90% of the microspheres in the sample for all but the sample B. Most samples have +/−20% variation, and one has +/−16% variation.

The swell capacity was measured for each of samples B through F using the procedure described in the General Methods. Each sample had a maximum swell that was greater than 70 grams of water per gram of microspheres, as shown in Table 5. The samples with larger sizes of microspheres, E and F, had a small increase in swell capacities above those of the smaller microsphere samples, but overall the microsphere size did not greatly affect the swell capacity.

TABLE 5

Water uptake in sieved microsphere samples.

| | Sample | | | | |
|---|---|---|---|---|---|
| | B | C | D | E | F |
| Swell (g H$_2$0/g microspheres) | 77.1 | 80.7 | 80.0 | 88.6 | 90.0 |

Example 5 (Comparative)

Comparative Example for Preparation of Hydrogel Microspheres

This example compares the properties of hydrogel microspheres prepared using the process described in present Example 1 with those of hydrogel microspheres prepared for comparison using the method of Example 2 of U.S. Pat. No. 6,218,440.

Following the method of Example 2 of U.S. Pat. No. 6,218,440, in a 1 L round-bottom flask equipped with an overhead stirrer, thermometer, reflux condenser, and nitrogen inlet was prepared a solution of 12.0 g ethyl cellulose and 590 g methylene chloride (solution A). The mixture was stirred at 250 rpm until the ethyl cellulose dissolved; and the agitator was then maintained at that speed to create a slight vortex. In a second flask, was prepared a solution of 0.50 g methyl cellulose, 1.00 g N,N'-methylenebisacrylamide, 8.67 g Triton™ X-405 (70% solution), and 49.8 g water (solution B). In a third separate flask was mixed 19.5 g acrylic acid and 19.5 g of a 25% aqueous sodium hydroxide solution (to reach a pH of between 5 and 6) (solution C). This acrylic acid solution was then added to the water solution B.

At this point, while rapidly stirring the mix of Solutions B and C, three separate solutions were prepared as follows: (a)

2.00 g of ammonium persulfate in 3.0 g of water (solution D); (b) 1.2 g of sodium hydrosulfide in 0.2 g of water (solution E); and (c) 1.2 g of Iron III chloride in 0.2 g of water (solution F).

While rapidly stirring the mix of solutions B and C, solution D was added and stirred for 5 min. The combined solution of B, C, and D was then added to the round-bottom flask containing solution A. After this addition, the remaining catalyst solutions E and F were added, and the reaction mixture was allowed to stir for an additional 20 h at room temperature. After this time approximately 350 mL of methanol was added to the reaction mixture, and the microspheres were allowed to stir for an additional hour. The resulting microspheres were then filtered and an additional 400 mL of methanol was then used to wash the microspheres. Again, the microspheres were filtered and washed with 700 mL of ethanol. They were then filtered again and placed in a vacuum oven set at 50° C. with a nitrogen purge. After drying, 34.5 g of a pinkish tan product in the form of microspheres was recovered.

Example 6

Microsphere Properties—Comparative Studies

Comparative studies were conducted with the microspheres produced as described in present Example 5 and a sample of microspheres prepared according to present Example 1. The Example 5 process microspheres were pink to tan, while the Example 1 process microspheres were white, as determined by visual inspection (Table 7).

Using the test for swelling in the General Methods, the microspheres prepared by the Example 5 process absorbed 46 g of water per g of microspheres, while the Example 1 process microspheres absorbed 98 g of water per g of microspheres.

Diameter ranges of microspheres in the samples were obtained via visual inspection of scanning electron micrographs set at low magnification in order to observe a high population of microspheres. The smallest and largest microspheres seen in each microsphere population were measured and were used as the top and bottom ranges for the diameter, as given in Table 7. The Example 5 microspheres had diameters ranging between 100 and 475 microns, while the Example 1 process microspheres had diameters between 25 and 250 microns. Note that in this present Example 6, a small sample of present Example 1 process microspheres was assayed, as compared to the sample analyzed in present Example 4, leading to a smaller range in sizes than shown in Table 4.

Bulk density was measured by filling a 50 cm³ tared graduated cylinder with microspheres to the 50 cm³ mark, tapping them down to ensure maximum packing density, and weighing the filled graduated cylinder. Bulk density was then determined by obtaining the weight of the microspheres by difference and dividing that weight by 50 to obtain a density value measured as g/cm³. The Example 1 process microspheres had a much greater density than the Example 5 process microspheres (Table 7).

Fracture of microspheres was tested as follows. A sample of 60 mg of microspheres, prepared as in Example 1 or as in Example 5, was added to 10 mL of either deionized water at pH=2.1 to prevent swell or at pH=7.0 to allow swell. Included in the water was 30 mg of acridine orange, a cationic dye used to stain the microspheres. Each sample of microspheres was filtered out using a micromesh particulate specimen bag, and suspended in 10 mL of solution with the same pH as the starting solution. Each sample was mixed by vortexing, and 2 mL was injected through either a 20 or 21 gauge needle. The injected samples were collected, and the size distribution of the resulting particles was analyzed using the Beckman-Coulter™ RapidVUE® particle analysis system described in Example 2. The injection experiment was repeated 3 times for each sample. As shown in Table 6, both types of unswelled microspheres (in acid solution) passed through 20 gauge and 21 gauge needles without fracture, since the average sample diameters remained constant within the variability of the assay. However, the average diameter of the swelled (in neutral solution) Example 5 type microspheres was greatly reduced after passing through 21 gauge (by about one-third) and 20 gauge (by almost half) needles. In contrast, the average diameter of the swelled (in neutral solution) Example 1 type microspheres was only slightly reduced after passing through 21 gauge and 20 gauge needles. Samples of the Example 5 type microspheres after passage through the 21 gauge needle were viewed by light microscopy. Fragments of microspheres were prevalent.

TABLE 6

Average diameters of microsphere samples following injections.

| | Delivery Solution | | | | | |
|---|---|---|---|---|---|---|
| | Acid | | | Neutral | | |
| | Needle size | | | | | |
| | none | 20G | 21G | none | 20G | 21G |
| Microspheres prepared as in Example 1 | | | | | | |
| Run Av. Diameter | 257 | 240 | 235 | 618 | 569 | 545 |
| Run Av. Diameter | 251 | 236 | 223 | 627 | 582 | 549 |
| Run Av. Diameter | 239 | 225 | 212 | 628 | 586 | 562 |
| Overall Av. Diameter | 249 | 234 | 224 | 624 | 579 | 552 |
| Std. Deviation | 10 | 8 | 11 | 5 | 9 | 9 |
| Microspheres prepared as in Example 5 | | | | | | |
| Run Av. Diameter | 252 | 258 | 298 | 623 | 367 | 403 |
| Run Av. Diameter | 238 | 252 | 269 | 632 | 371 | 422 |
| Run Av. Diameter | 226 | 252 | 256 | 644 | 384 | 425 |
| Overall Av. Diameter | 239 | 254 | 274 | 633 | 374 | 417 |
| Std. Deviation | 13 | 4 | 22 | 11 | 9 | 12 |

Microsphere density was measured by the following density gradient technique. A continuous density gradient was established in a vertical column. The gradient was established by partially mixing the column with layers of solvent having different densities. In this case heptane ($d^{20}_4$=0.684) and carbon tetrachloride ($d^{25}_{25}$=1.589) were mixed using different ratios to obtain low and high density mixtures. Then these mixtures were once again mixed through a nitrogen purge system to produce a density blend.

A sample of microspheres was introduced into the gradient, and the microspheres reached an equilibrium point after 24 h, where the density of the liquid equaled the microsphere density. The gradient tubes were temperature controlled at 25° C. Calibrated floats of known densities were used to calibrate the gradient tube in terms of position vs. density. The density of the microspheres was determined using a focusable calibrated magnifying eyepiece to identify the measurable difference between the calibrated float and the sample microspheres, which allowed for a direct conversion to a microsphere density value as given in Table 7. A portion of Example 5 microspheres floated at the top of the gradient indicating a density of less than 0.8 g/cm³, which was not measurable in the system used.

Figure 6A:
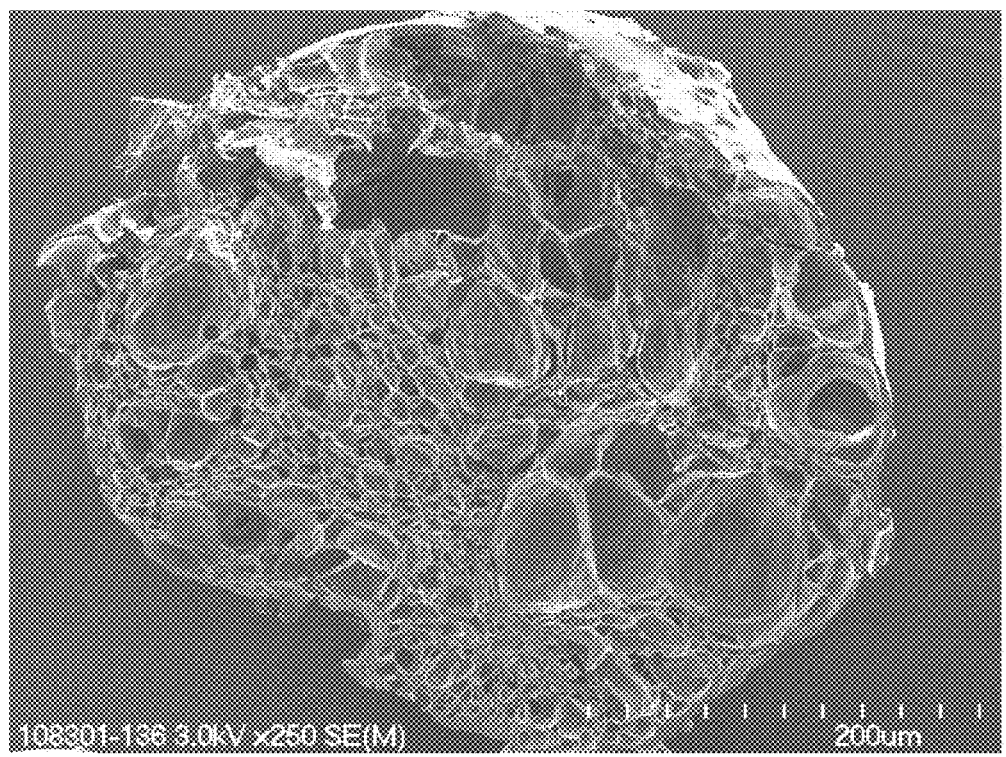
FIG. 6 shows SEM cross sections of: A) an open cell porous microsphere as prepared using the process of Example 5, and B) a closed cell pore microsphere as prepared using the process of Example 1.
Figure 6B:
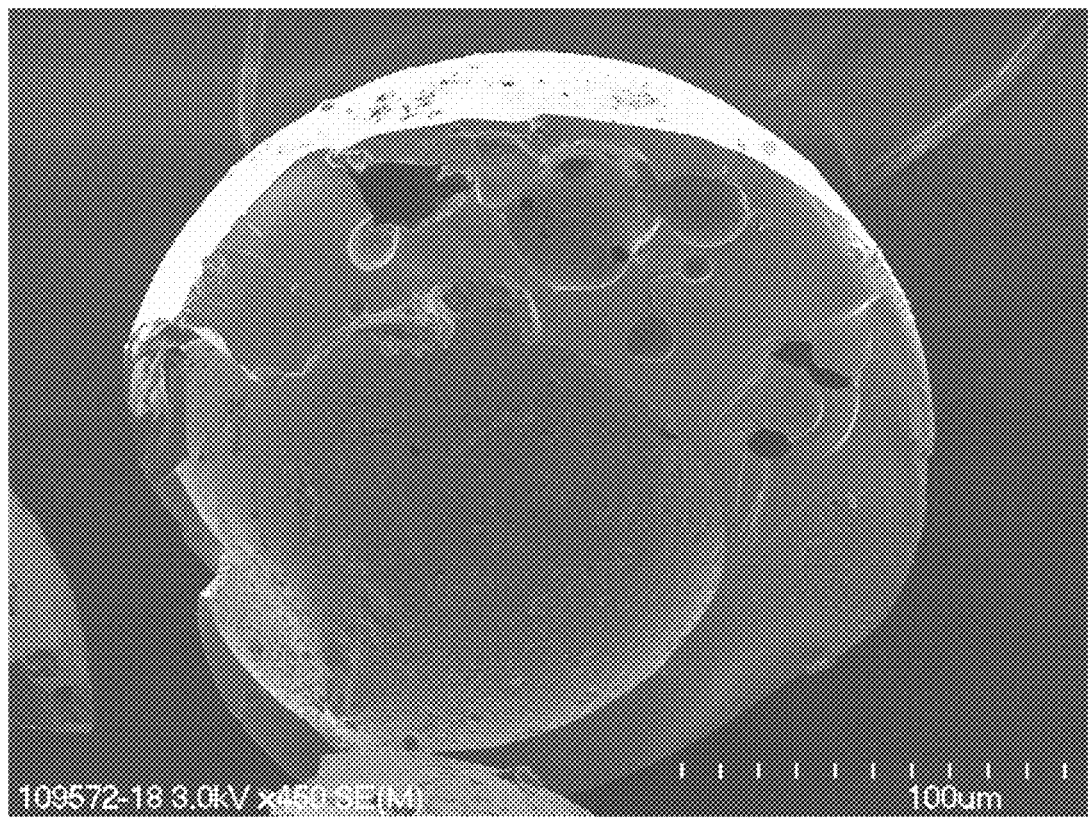
Figure 7A:
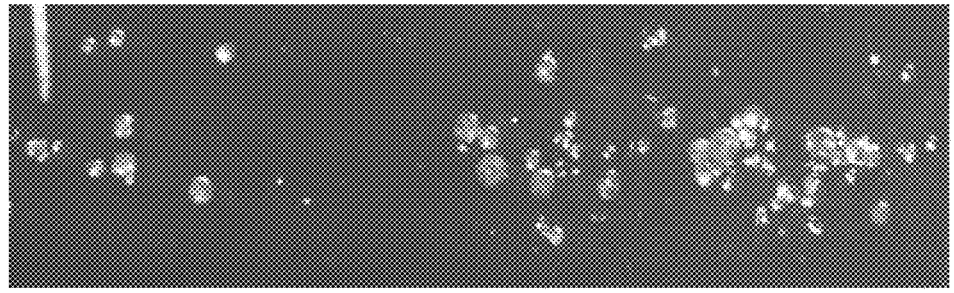
FIG. 7 shows the original photographs upon which the drawings of FIG. 1 are based.
Figure 7B:
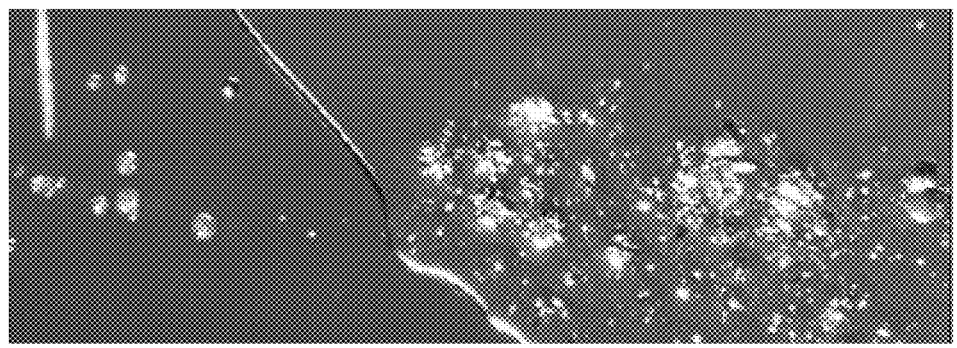
Figure 7C:
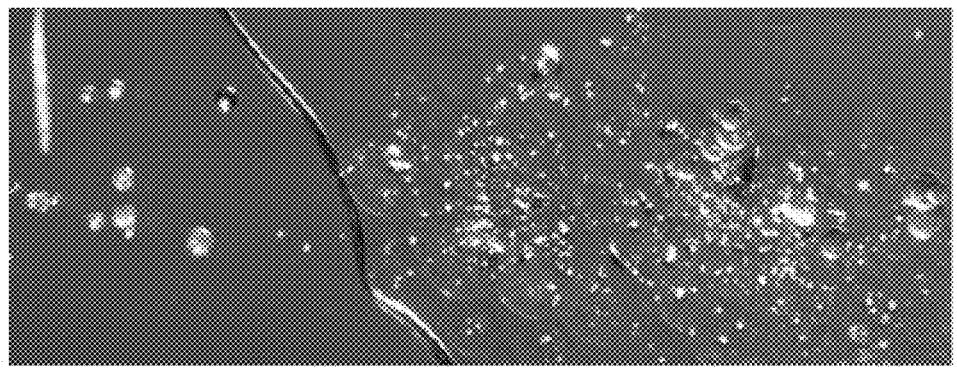

Cross sections of microsphere samples were obtained through standard cutting and microtoming techniques. The microsphere cross sections were examined using standard scanning electron microscopy techniques. As seen in the micrographs of FIG. 6, the Example 5 process microspheres were extremely porous (FIG. 6A) while the Example 1 process microspheres contained closed cell voids in relatively low numbers (FIG. 6B). This visual characteristic of extent of porosity is consistent with the density and fracture characteristics of the two different microsphere samples.

TABLE 7

Comparative properties of Example 5 process and Example 1 process microspheres.

| Property | Example 5 Process Microspheres | Example 1 Process Microspheres |
| --- | --- | --- |
| Color | pink to tan | white |
| Swell Capacity | 46 g water/g microspheres | 98 g water/g microspheres |
| Diameter Range | 100-475 microns | 25-250 microns |
| Bulk Density (dry) | 0.182 g/cm$^3$ | 0.680 g/cm$^3$ |
| Microsphere density | 0.80 g/cm$^3$ or less | 1.54 g/cm$^3$ |
| Durability of swelled microspheres | fracture in moving through 20 gauge needle | do not fracture in moving through 20 gauge needle |

It can be observed clearly from this comparative example that the present preparative method for hydrogel microspheres described in Example 1 produces more compact, denser, more spherical microspheres, which can swell up to 2× better than microspheres produced using the method of comparative Example 5.

In addition, microspheres prepared by the process of Example 1 are able to deform following swell. Onto a glass microscope slide was placed a group of dry microspheres prepared as in Example 1. The microspheres were covered with a second glass microscope slide and pressure was applied by pressing the top slide against microspheres and the bottom slide by hand, while observing the microspheres under a microscope. When the dried microspheres were pressed in this manner, no noticeable deformation of the microspheres was observed. At this point water was added in sufficient quantity to fully hydrate the microspheres causing them to swell. Pressure was again applied as previously described. When observed under the microscope the microspheres were seen to readily deform under the pressure to a point where it appeared that they were very flat. Upon release of the pressure, the microspheres immediately regained their original spherical shape. Microspheres prepared according to the Example 5 process begin to deform and then fracture when treated with the same pressure.

Example 7

Sterilization of Swellable/Deformable Microspheres

Individual samples of microspheres prepared as in Example 1 were exposed to either ethanol for 15 min, to 260 nm ultraviolet (UV) light for 30 min, or to gamma radiation at about 28 kGy. In all cases, the resulting sterilized microspheres exhibited similar expansion coefficients to non-sterilized microspheres when exposed to neutral water, indicating that no additional crosslinking or other negative processes had occurred during the sterilization processes.

Example 8

Direct Cell Contact Testing to Assess Cytotoxicity of Swellable/Deformable Microspheres NIH3T3 human fibroblast cells (obtained from the ATCC, # CRL-1658) were grown in Dulbecco's modified essential medium (DMEM), supplemented with 10% fetal calf serum. A cell culture was challenged with 10 mg of microspheres prepared as in Example 1 according to FDA standard procedure ISO10993-5:1999. The microsphere sample was coated on the bottom of a well in a polystyrene culture plate. The well was then sterilized under UV light and seeded with 50,000-100,000 NIH3T3 cells. The cell culture was incubated for 48 h. The cells grew normally confluent and coated the well bottom, growing up to the edges of the microspheres. This result demonstrated a lack of cytotoxicity of the microspheres.

Example 9

Macrophage Activation Testing to Assess Inflammatory Potential of Swellable/Deformable Microspheres The testing was done using J774 Macrophage cultures according to FDA standard procedure ISO10993-5:1999. The J774 Macrophage cells were obtained from ATCC (# TIB-67) and were grown in DMEM supplemented with 10% fetal bovine serum.

A J774 mouse peritoneal macrophage cell culture was challenged with 10 mg of microspheres prepared as in Example 1. The microsphere sample was coated on the bottom of a well in a polystyrene culture plate. The well was then sterilized under UV light and seeded with J774 cells. The cell culture was incubated for 48 h. The cell culture was then analyzed for TNF-α (tumor necrosis factor alpha), an indicator of inflammatory response, using an ELISA assay, as described by Lara et al. (*Journal of Dental Research* 82(6): 460-465, 2003). The assay was carried out using a kit purchased from R&D systems (catalog #MTA00), which utilizes a polyclonal antibody against mouse TNF-α. The TNF-α titer was similar to the negative control (a blank well), which indicated the non-inflammatory nature of the microspheres.

Example 10

Hemolysis Testing to Assess Hemocompatibility of Swellable/Deformable Microspheres The testing was done using human red blood cells according to FDA standards (ISO10993-4:2002 standards). The red blood cells were obtained from human donors and were diluted to a 5% solution of red blood cells in phosphate buffered saline (1× concentration, pH 7.4).

Dilutions of microspheres prepared as in Example 1 were made in phosphate buffered saline at concentrations of 4.0 μg/mL to 500 μg/mL. The red blood cells were challenged with the microsphere samples by incubating 500 μL of each microsphere solution with 25 μL of 5% red blood cells. The red blood cells with microspheres were incubated for 30 min with agitation. The red blood cells were then analyzed for hemolysis, using spectrophotometry, as described by Malinauskas (*Artificial Organs* 21(12):1255-1267, 1997).

The extent of hemolysis was determined by measuring hemoglobin release from lysed red blood cells. The amount of hemoglobin released by the sample was measured spectrophotometrically at 540 nm. The hydrogel microspheres induced 0.0% hemolysis at a microsphere concentration of 500 μg/mL. This indicated the non-hemolytic nature of the microspheres.

Example 11

Expansion of Swellable/Deformable Microspheres in Whole Blood

Whole blood was extracted from a rabbit and stored in a 15 mL polypropylene tube (Falcon tube). The microspheres prepared as in Example 1 were suspended in the blood approximately 30 min after it was taken from the rabbit. At this time, some minimal amount of clotting was visible in the blood sample. A 10 mg sample of microspheres was suspended in a 5 mL blood sample for 3 min and then observed under a light microscope. The exposed microspheres exhibited similar expansion coefficients (see Example 13) to microspheres that were exposed to neutral water, demonstrating that the microspheres suspended in whole blood had a similar swelling response to those in pure water. Additionally, the time-course of the swelling was approximately the same; the spheres swelled fully in whole blood in seconds.

Example 12

Determination of Appropriate DMSO levels for Delivery of Unswelled Microspheres

Solutions containing different concentrations of DMSO were tested for their effect in maintaining the swellable/deformable microspheres prepared as described in Example 1 in an unswelled state. The solutions containing different amounts of DMSO and water listed in Table 8 were prepared in nine separate 0.5 mL Eppendorf test tubes.

TABLE 8

Solutions with varying DMSO concentration.

| Experiment | DMSO (μL) | Water (μL) | % Water in Mix |
|---|---|---|---|
| 1 | 100 | 0 | 0 |
| 2 | 100 | 20 | 16.7 |
| 3 | 100 | 60 | 37.5 |
| 4 | 100 | 100 | 50 |
| 5 | 100 | 150 | 60 |
| 6 | 100 | 200 | 66.7 |
| 7 | 100 | 300 | 75 |
| 8 | 100 | 400 | 80 |
| 9 | 0 | 400 | 100 |

To each test tube was added 5 mg of the swellable/deformable microspheres prepared in Example 1. Each tube was then briefly shaken to submerge all of the microspheres, and they were each left to stand for at least 3 min to allow complete microsphere swelling. At this point samples from each tube were taken and imaged under a microscope at 5× magnification. The level of swell of the microspheres in each tube was qualitatively compared. The comparison showed that solutions containing a high concentration of DMSO (solutions 1-3) effectively suppressed microsphere swell. The solution containing 50% water (solution 4) caused very significant swelling of the microspheres, and solutions containing a higher percentage of water (solutions 5-9) produced about the same level of swell in the microspheres as with 50% water.

Example 13

Determination of Effect of pH for Delivery of Unswelled Microspheres

Three solutions of differing pH were prepared by adding HCl and/or NaOH to water and quantifying the resulting pH with a pH meter. Solutions of pH 2.0; 7.1, and 10.2 were prepared. At this point individual microspheres prepared as described in Example 1 were isolated on a microscope cover slide in their unswelled state. An image of the dry microsphere was recorded at 20× magnification, and the diameter of the microsphere was measured and recorded. A drop (enough to saturate the microsphere) of one of the aqueous solutions of known pH was then added to the microsphere. The hydrated microsphere was then imaged under a microscope at 5× magnification, and the diameter at the widest point was measured and recorded. The volumetric expansion coefficient was then calculated for the microsphere following hydration using the following equation: volume of hydrated microsphere/volume of dry microsphere=volumetric expansion coefficient. This was calculated as follows:

$$4/3\pi(d_{hyd}/2)^3 / 4/3\pi(d_{dry}/2)^3$$

where $d_{hyd}$=diameter of the hydrated microsphere and $d_{dry}$=diameter of the dry microsphere Each set of conditions was repeated 5 times with a new microsphere each time. The results, shown in Table 9, demonstrated that in an acidic pH solution, the microspheres underwent almost no swell.

TABLE 9

Effect of pH on microsphere swell.

| | Solution pH | | |
|---|---|---|---|
| | 2.0 | 7.1 | 10.2 |
| Average Expansion Coefficient | 1.18 | 85.85 | 73.91 |
| Standard Dev. | 0.12 | 20.98 | 23.75 |

Example 14

Evaluation of Contrast Agents MD-76® and Ethiodol® as Media for Delivery of Swellable/Deformable Microspheres A single dry microsphere from a preparation described in Example 1 was isolated on a microscope slide and imaged at 10× magnification. The diameter was recorded. Approximately 0.25 mL of contrast medium MD-76® (supplied by Tyco; Mansfield, Mass.) was added directly to the slide, suspending the microsphere. A time of 3 min was allowed for microsphere/contrast contact. The microsphere was then imaged again using a microscope at 5× magnification, and the diameter was recorded. The volumetric expansion coefficient of the microsphere was computed as described in Example 13. The suspending and measurement process was then repeated an additional 5 times. The average expansion coefficient of microspheres suspended in MD-76® was 4.9, with a range of between 3.6 and 7.4. Experiments were repeated using neutral water in place of MD-76®. From these experiments an average expansion coefficient of 117.5 was obtained, with a range of between 88 and 146.

The experiment was repeated using Ethiodol® (supplied by SAVAGE Laboratories®; Melville, N.Y.). The expansion coefficients of the microspheres in Ethiodol® were lower than those obtained for microspheres in MD-76® as determined by visual inspection.

Example 15

Passage of Swellable/Deformable Microspheres Through Catheters Using DMSO

Microspheres prepared as described in Example 1 with an average dry diameter of approximately 250 microns were suspended in DMSO by mixing in a 60 mL Falcon Tube for 3 min with a Vortex Touch Mixer (speed 10). Suspensions consisted of 2000 mg of the microspheres in 8 mL (250 mg/mL), or 5 mL (400 mg/mL) of DMSO. An attempt was made to inject 2.5 mL of each suspension through each of various sized catheters using a 10 mL syringe. The following catheters were used: a Cordis Vistabritetip guiding catheter (7 F), a Medtronic A VE $Z^2$ guiding catheter (6 F), and a Cordis PTA dilation catheter, Opta 5 (5 F). The 250 mg/mL suspension readily passed through the Medtronic A VE $Z^2$ guiding catheter (6 F) and the Cordis Vistabritetip guiding catheter (7 F). However, this suspension did not pass through the Cordis PTA dilation catheter, Opta 5 (5 F). The microspheres aggregated around the entry point of the lumen of the 5 F catheter. The 400 mg/mL suspension was not able to pass through any of the catheters. This solution could not even maintain homogeneity when injected from the 10 mL syringe with no associated catheter, which indicated an over saturation of microspheres in DMSO, Thus this represents an upper limit of concentration for the microspheres, regardless of catheter dimensions.

The microspheres that were passed through the 6 F catheter at 250 mg/mL were collected and observed under a light microscope at 10× magnification. No difference in the level of fragmentation was observed for passed microspheres when compared to controls. Passage of the microspheres through the catheter had no visible adverse effects on the physical integrity of the microspheres.

Example 16

Passage of Swellable/Deformable Microspheres Through a 5 F Catheter

Two samples of microspheres prepared as described in Example 1 were further prepared as in Example 15. The first sample was prepared using 750 mg of microspheres with an average dry diameter near 250 microns and 5 mL of contrast medium MD-76® (150 mg/mL). The second sample was prepared using 1500 mg of microspheres with an average dry diameter of approximately 100 microns, prepared by sieving as described in Example 4, and 5 mL of contrast medium MD-76® (300 mg/mL). Both suspensions readily passed through a Cordis PTA dilation catheter, Opta 5 (5 F). As determined in Example 14, the microspheres had an average expansion coefficient of 4.9 in MD-76®.

Example 17

In-Vivo Occlusion of Porcine Vasculature with Swellable/Deformable Microspheres

Suspensions of microspheres that were made as described in Example 1 were further prepared by adding 200 to 1000 mg of microspheres to 5 mL of DMSO in a 15 mL Falcon tube. The suspensions were made 48 h before administration. The porcine studies were conducted on three separate days using adult male pigs. A 12 mL syringe was used to inject each prepared suspension through a 6 F catheter. Prior to each attempted injection, the catheter was angiographically guided to the target location. The injection medium and the targeted vasculature for each experiment are summarized in Table 10.

TABLE 10

In vivo experiments.

| Experiment | Microsphere Mass (mg) | Dilution | Volume Delivered (mL) | Vessel/Organ | Chase (10 mL) |
|---|---|---|---|---|---|
| 1 | 200 | none | 4.5 | R. Kidney/Renal Artery | DMSO |
| 2 | 500 | none | 5.0 | L. Kidney/Superior Branch of Renal Artery | DMSO:Saline 9:1 |
| 3 | 1000 | 3 mL DMSO | 6.0 | Heart/Right Coronary Artery | DMSO:Saline 9:1 |

The targeted vasculature was readily located in all attempted injections. The low viscosity of the delivery media facilitated passage of the microspheres through the catheter. Following the injection of the microspheres, contrast medium was injected to angiographically determine if the target vessel had been occluded (diversion of contrast indicated vessel occlusion). Imaging clearly showed blockage of blood flow distal to the target site in each experiment. Dissection of the renal artery showed an occlusion formed by swelled microspheres at the target site. The microspheres successfully occluded porcine renal vasculature and the porcine right coronary artery.

Example 18

Tube Occlusion with Swellable/Deformable Microspheres and Quantification of Internal Pressure Required to Dislodge Occlusion A linear connected tube system consisting in order of a 60 mL syringe, an 80 cm length tube with an in-line clinical grade pressure transducer (#72-4496; Harvard Apparatus) in the center, and a detachable 1.58 mm internal diameter Tygon® tube (AAB00003 B-44-3 Beverage tubing, #TBT-062B, Small Parts, Inc., Miami Lakes, Fla.) was used to test the durability of occlusions formed by microspheres prepared as described in Example 1. This Tygon® tube has an outside diameter of 4.76 mm and a wall thickness of 1.59 mm. The tube with the in-line transducer was AAB00009 B-44-3 Tygon® tubing, which was connected on one end to the syringe, and on the other end to the AAB00003 B-44-3 Tygon® tubing through a step down connector (STCR-09/16, Small Parts, Inc., Miami Lakes, Fla.). The AAB00003Tygon® tube was detached from the system and filled with a 2.5 mL aqueous suspension containing various weights (dry weight) of microspheres (250-500 microns dry diameter) as listed in Table 11. The tube was reattached. The syringe was used to gradually impart internal pressure to the Tygon® tube. The pressure needed to dislodge the microspheres from the Tygon® tubing was recorded as readings from the pressure transducer. The results are given in Table 11.

TABLE 11

Dislodging pressure for swellable/deformable microsphere occlusions in vitro.

| Run # | Dry Mass Swellable Hydrogel Microspheres (mg) | Resulting Pressure Recorded (mm Hg)/ (kPa) |
|---|---|---|
| 1 | 15 | 140/(18.7) |
| 2 | 15 | 114/(15.2) |
| 3 | 15 | 126/(16.8) |
| 1 | 18 | 570/(76.0) |
| 2 | 18 | 660/(88.0) |
| 3 | 18 | 588/(78.4) |
| 1 | 20 | max (>1000/133) |
| 2 | 20 | max (>1000/133) |
| 3 | 20 | max (>1000/133) |

Microsphere occlusions were able to withstand over 1,000 mm Hg (133 kPa) of pressure. The results of this study demonstrated that the swellable/deformable microspheres are capable of occluding high flow, low resistance systems. This system closely models the most difficult scenario to occlude, arterio-venous malformations due to the relatively large diameter of the Tygon® tube. In most other potential applications vessel diameter is constantly reduced in the target tissue, which virtually guarantees occlusion at some level in the vascular tree.

Example 19 (Comparative)

Comparative Tube Occlusion with Non-Swellable Hydrogel Microspheres and Quantification of Internal Pressure Required to Dislodge Occlusion As a comparison, the durability of occlusions formed by microspheres having almost no swell capacity was tested as described in Example 18. These microspheres were those prepared as Sample 9 in Example 2, having a swell capacity of 1.5 gram of water per gram of microspheres which is considered to be non-swellable. The Tygon® tube was detached from the system and filled with a 2.5 mL aqueous suspension containing various weights (dry weight) of the highly crosslinked microspheres (250-500 microns dry diameter, as listed in Table 12. A syringe was used to gradually impart internal pressure to the Tygon® tube. The pressure needed to dislodge the microspheres from the Tygon® tubing is shown in Table 12 for each sample.

TABLE 12

Dislodging pressure for non-swellable microsphere occlusions in vitro.

| Run # | Dry Mass Non-Swellable Hydrogel Microspheres (mg) | Resulting Pressure Recorded (mm Hg)/ (kPa) |
|---|---|---|
| 1 | 20 | <15 (2.0) |
| 2 | 20 | <15 (2.0) |
| 3 | 20 | <15 (2.0) |
| 1 | 100 | <18 (2.4) |
| 2 | 100 | <15 (2.0) |
| 3 | 100 | <15 (2.0) |
| 1 | 500 | 43 (5.7) |
| 2 | 500 | 66 (8.8) |
| 3 | 500 | 37 (4.9) |

In this example the non-swellable nature of the microspheres does not allow for tight packing of the microspheres and extremely inefficient occlusion is achieved, as determined by the low pressure that is adequate to dislodge the occlusion.

Example 20

Delivery of Swellable/Deformable Microspheres Sufficient for Occlusion through a 3 F Microcatheter Four different suspensions of the microspheres of Example 1 were prepared as the following samples:
1) 1 mL wet volume (corresponds roughly to 10 mg dry mass) diluted to 6 mL with phosphate buffered saline (0.138 M NaCl, 0.0027 M KCl pH 7.4) within a 6 mL syringe. These microspheres are fully swelled.
2) 10 mg dry mass suspended in 6 mL of 0.3 g/mL sodium chloride in water within a 6 mL syringe. This concentration of sodium chloride limits swell.
3) 30 mg dry mass suspended in 6 mL of 0.3 g/mL sodium chloride in water within a 6 mL syringe.
4) 60 mg dry mass suspended in 6 mL of 0.3 g/mL sodium chloride in water within a 6 mL syringe.
5) 120 mg dry mass suspended in 6 mL of 0.3 g/mL sodium chloride in water within a 6 mL syringe.

Each suspension was injected through a separate 3 F Renegade® Fiber braided microcatheter which has a 533 micron inner diameter (Lot # 7704153, Boston Scientific, Natick, Mass.). The tip of each microcatheter was placed into a beaker to monitor for any effluent. For all injections, the syringe was constantly agitated to ensure adequate mixing.

From the sample 1 suspension containing swelled microspheres, some microspheres were able to pass through the Renegade® microcatheter, but the vast majority, greater than 95%, remained within the syringe. The sample 2, 3, and 4 suspensions of limited swell microspheres passed through the microcatheters completely. The sample 5 suspension allowed some passage of microspheres, but the microcatheter became blocked after approximately 3 mL of the suspension was delivered. This experiment demonstrated that amounts of 10 mg, 30 mg, and 60 mg of limited swell microspheres were able to pass through a 3 F catheter having an inner diameter of 533 microns. Thus a 3 F catheter may be used to deliver an amount of swellable/deformable microspheres that is sufficient to form a highly durable occlusion as tested in Example 18.

Example 21

Preparation of Microspheres Containing Barium as an Imaging Agent

Into a 1 L round-bottom, three-necked flask equipped with an overhead stirrer, thermometer, reflux condenser, and nitrogen inlet port was prepared a solution of 12.0 g ethyl cellulose, 400 mL chloroform, and 190 g methylene chloride (solution A). The mixture was stirred at 160 rpm until the ethyl cellulose dissolved; then the agitator was increased in speed to 250 rpm to create a slight vortex. In a second flask, was prepared a solution of 0.50 g methyl cellulose, 1.00 g N,N'-methylenebisacrylamide, 8.67 g Triton X-405 (70% solution), and 49.8 g water (solution B). In a third separate flask was mixed 19.5 g acrylic acid, 4.0 g barium hydroxide, and 16.4 g of a 25% aqueous sodium hydroxide solution (to reach a pH of between 5 and 6), and 10 mL of water (solution C). This acrylic acid solution was then added to the water solution B.

At this point, while rapidly stirring the mix of Solutions B and C, 0.05 g of the water-soluble VA-044 initiator (2,2'-azobis(2-1[2-imidazolin-2-y])propane dihydrochloride) was added and the resulting solution was stirred for 5 min. This solution (the "first solution") was then added to the round-bottom flask containing solution A (the "second solution"). The reaction mixture was allowed to stir at 250 rpm for about 1 h at room temperature, forming the "first suspension". The first suspension was then heated to 51° C. and stirred at 250 rpm for an additional 5.5 h at that temperature, and another 15 h at room temperature, forming the "second suspension". After this time, approximately 400 mL of methanol was slowly added to the second suspension and the microspheres were allowed to stir an additional hour. The microspheres were then filtered and washed with an additional 250 mL of methanol. They were filtered again and finally washed with 250 mL of ethanol. They were then dried in a nitrogen purged vacuum oven set at 100° C.

The resulting microspheres were white in color. The final yield of dried microspheres was 23.1 g. When exposed to water, the microspheres absorbed 86 g of water/g of microspheres. An X-ray imaging analysis clearly indicated that Barium was contained within the microsphere structure allowing excellent imaging of individual microspheres when dry. As the microspheres swelled, the Barium density was diluted so that imaging became more difficult.

Example 22

Delivery of Swellable/Deformable Microspheres in DMSO through a 3 F Microcatheter The microspheres of Example 1 were suspended in DMSO at concentrations of 10 mg/mL, 30 mg/mL, and 60 mg/mL. Six milliliters of each suspension was loaded into a syringe and injected through a separate 3 F Renegade® Fiber braided microcatheter which has a 533 micron inner diameter (Lot # 7704153, Boston Scientific, Natick, Mass.). The tip of each microcatheter was placed into a beaker to monitor for any effluent. For all injections, the syringe was constantly agitated to ensure adequate mixing. Using the 10 mg/mL suspension, microspheres passed through the catheter into the beaker, as observed by adding water to the collection beaker. Some microspheres adhered to the walls and plunger of the syringe, most likely caused by static electricity due to the dryness of the air. Similar results were obtained using the 30 mg/mL suspension, with some microspheres passing through the catheter and some adhering to the syringe. Using the 60 mg/mL suspension, the catheter became occluded after a couple milliliters of DMSO passed through the catheter. A control suspension of 10 mg/mL microspheres in water (fully swelled) occluded the catheter immediately, and the occlusion was visible at the entry point of the catheter.

Example 23

Preparation of Swellable Microspheres Using Methacrylic Acid

In a 1 L round-bottom, three-necked flask equipped with an overhead stirrer, thermometer, reflux condenser, and nitrogen inlet port was prepared a solution of 6.0 g of ethyl cellulose, 200 mL of chloroform, and 95 g of methylene chloride (solution A). The mixture was stirred at 180 rpm until the ethyl cellulose dissolved. In a second flask, was prepared a solution of 0.25 g of methyl cellulose, 0.419 g of N,N'-methylenebisacrylamide (2.4 Mol % of monomer), 4.335 g of Triton™ X-405 (70% solution), and 26.22 g of water (solution B). In a third separate flask was mixed 9.75 g of methacrylic acid and 9.06 g of a 25% aqueous sodium hydroxide solution (to reach a pH of between 5 and 6) (solution C). This methacrylic acid solution was then added to solution B.

At this point while rapidly stirring the mixture of Solutions B and C, 0.025 g of the water-soluble azo initiator VA-044 initiator (2,2'-azobis(2-[2-imidazolin2-yl])propane dihydrochloride) was added, and the resulting solution was stirred for 5 min to form the "first solution". The first solution was then added to the round-bottom flask containing solution A (the "second solution"). The resulting reaction mixture was stirred at 412 rpm for about 1.5 h at room temperature, forming the "first suspension". The stirring speed was reduced to 225 rpm and the first suspension was heated to 51° C. The first suspension was maintained at the same stirring rate and temperature for almost 6 h to allow for substantial microsphere formation, (i.e., the "second suspension"). The second suspension was then stirred at 225 rpm for another 14 h at room temperature to ensure complete polymerization. After this time, approximately 250 mL of methanol was slowly added to the suspension to remove water from the microspheres, and the microspheres were allowed to stir an additional hour. The microspheres were then filtered, washed with an additional 75 mL of methanol, filtered again, and finally washed with 75 mL of ethanol. The microspheres were then dried in a nitrogen purged vacuum oven set at 100° C. The resulting microspheres were white in color. The final yield of dried microspheres was 7.8 g.

The resulting dried microspheres exhibited diameters generally ranging from 40 microns to 150 microns as measured from photos acquired using scanning electron microscopy. Microsphere swell was tested as described in General Methods. When exposed to water, the microspheres absorbed 98 g of water/g of microspheres.

Example 24

Preparation of Swellable Microspheres using a Combination of Phenylethyl Acetate, Ethyl Heptanoate, and Methylene Chloride as Solvent In a 1 L round-bottom, three-neck flask equipped with an overhead stirrer, thermometer, reflux condenser and nitrogen inlet, was prepared a solution of 12.0 g of ethylcellulose (Aldrich No. 200646), 280 mL of phenylethyl acetate (Aldrich No. 290580), 120 mL of ethyl heptanoate (Aldrich No. 112364) and 190 mL of methylene chloride (EMD No. DX0831-6). The mixture was stirred at a rate of 360 rpm until all of the ethylcellulose dissolved, making solution A. In a second flask, a solution was prepared containing 0.50 g of methylcellulose (Aldrich No. 274429), 49.8 g of water, 1.0 g of N,N methylenebisacrylamide (Aldrich No. 146072) and 8.67 g of Tritron X-405 (70% wt solution in water; Aldrich No. 234737), making solution B. In a third separate flask, 19.5 g of acrylic acid and 22.0 g of 25 wt % aqueous sodium hydroxide solution were mixed. The sodium hydroxide solution was added slowly using a pipette while the acrylic acid was stirred in an ice bath, making solution C.

The acrylic acid solution C was added to the water/methylcellulose solution B while vigorously stirring. Then, 0.025 g of the water soluble VA-044 initiator was added. The solution was stirred for 5 min forming the "first solution". Then, the first solution was added to the ethylcellulose solution A ("second solution"). The reaction mixture was stirred at room temperature for 1 h at 360 rpm forming the "first suspension". Then, the suspension was heated to 55° C. for 4 h with stirring at 360 rpm, forming the "second suspension". After this time the second suspension was stirred at 200 rpm overnight at room temperature. The next day, 400 mL of methanol was added using a dropping funnel and stirring was continued for 1 h at room temperature. Microspheres formed during this process were collected by filtration, washed with methanol, washed several times with ethanol, and then dried for 3 days in a vacuum oven at 100° C. with a slight nitrogen purge. The final yield of dried, white microspheres was 24.84 g.

Microsphere swell was tested as described in General Methods. When exposed to water, the microspheres absorbed 82.8 g of water/g of microspheres.

Example 25 (Comparative)

Preparation of Low Swell Microspheres Using Acrylamide as a Single Monomer

In a 1 L round-bottom, three-necked flask equipped with an overhead stirrer, thermometer, reflux condenser, and nitrogen inlet port was prepared a solution of 6.0 g of ethyl cellulose, 200 mL of chloroform, and 72 mL of methylene chloride (solution A). The mixture was stirred at 250 rpm until the ethyl cellulose dissolved. In a second flask, was prepared a solution of 0.25 g methyl cellulose, 0.51 g of N,N'-methylenebisacrylamide (2.4 Mol % of monomer), 4.335 g of Triton™ X-405 (70% wt solution in water), and 19.0 g of water (solution B). In a third separate flask was mixed 9.75 g of acrylamide and 14.0 g of water (the observed pH was between 5 and 6) (solution C). This acrylamide solution was then added to the crosslinker solution.

Then, while rapidly stirring the mixture of Solutions B and C, 0.025 g of the water-soluble azo initiator VA-044 (2,2'-azobis(2-[2-imidazolin2-yl])propane dihydrochloride) was added, and the resulting solution was stirred for 5 min, forming the "first solution". The first solution was then added to the round-bottom flask containing solution A (the "second solution"). The resulting reaction mixture was allowed to stir at 244 rpm for about 1 h at room temperature, forming the "first suspension". The stirring speed was reduced to 225 rpm and the suspension was heated to 49° C. with continued stirring for almost 6 h to allow for substantial microsphere formation (the "second suspension"). The second suspension was then stirred at 224 rpm for another 14 h at room temperature to ensure complete polymerization. After this time, approximately 250 mL of methanol was slowly added to the suspension to remove water from the microspheres, and the microspheres were stirred an additional hour. The microspheres were then filtered and washed with an additional 175 mL of methanol. They were filtered again, washed twice with 150 mL of ethanol, and dried in a nitrogen purged vacuum oven set at 100° C. The resulting microspheres were white in color. The final yield of dried microspheres was 11.2 g.

The resulting dried microspheres exhibited diameters generally ranging from 10 microns to 170 microns as measured from photos acquired using scanning electron microscopy. Microsphere swell was tested as described in General Methods. When exposed to water, the microspheres absorbed 5 g of water/g of microspheres.

Microspheres were prepared using N-hydroxymethyl acrylamide as monomer using a similar procedure. The resulting microspheres absorbed 6 g of water/g of microspheres.

These results suggest that when acrylamide or N-hydroxymethyl acrylamide are used as single monomers, microspheres with low swell are obtained. However, when these monomers are used as a co-monomer with acrylic acid, high swell microspheres are produced, as shown in Examples 26 and 27.

Examples 26 and 27

Preparation of Swellable Microspheres Using Acrylic Acid and Acrylamide as Co-Monomers In a 1 L round-bottom, three-necked flask equipped with an overhead stirrer, thermometer, reflux condenser, and nitrogen inlet port was prepared a solution of 6.0 g of ethyl cellulose, 200 mL of chloroform, and 72 mL of methylene chloride (solution A). The mixture was stirred at 250 rpm until the ethyl cellulose dissolved. In a second flask, was prepared a solution of 0.25 g methyl cellulose, 0.50 g N,N'-methylenebisacrylamide (2.4 Mol % of total amount of monomers), 4.335 g Triton™ X-405 (70% wt solution in water), and 25.3 g of water (solution B). In a third separate flask was mixed 8.775 g of acrylic acid and 9.74 g of a 25% aqueous sodium hydroxide solution (solution C). To this solution 0.975 g of acrylamide was added to generate a co-monomer solution with 90% acrylic acid and 10% acrylamide by weight (the pH was observed to be between 4 and 5). The experiment was repeated using a co-monomer ratio of 70% acrylic acid and 30% acrylic acid. The amount of NaOH and the crosslinker were changed to accommodate the monomer ratios, as shown in Table 13. This monomer solution was then added to the water solution (solution B).

TABLE 13

Experimental conditions for preparation of acrylic acid-acrylamide microspheres

| Example | % Acrylic Acid/ % Acrylamide | Crosslinker (g) | Acrylic Acid (g) | NaOH (mol) | Acrylamide (g) | Stirring Rate (rpm) |
|---|---|---|---|---|---|---|
| 26 | 90/10 | 0.500 | 8.775 | 0.061 | 0.975 | 325 |
| 27 | 70/30 | 0.503 | 6.825 | 0.047 | 2.925 | 335 |

Then while rapidly stirring the mixture of Solutions B and C, 0.025 g of the water-soluble azo initiator VA-044 (2,2'-azobis(2-[2-imidazolin2-yl])propane dihydrochloride) was added, and the resulting solution was stirred for 5 min, forming the "first solution". The first solution was then added to the round-bottom flask containing solution A (the "second solution"). The resulting reaction mixture was stirred (see Table 13 for stirring rates) for about 1 h at room temperature, forming the "first suspension". The stirring speed was reduced to about 225 rpm and the suspension was heated to 50.5° C. with continued stirring for almost 6 h to allow for substantial microsphere formation (i.e., the "second suspension"). The second suspension was then stirred at 225 rpm for another 14 h at room temperature to ensure complete polymerization. After this time, approximately 250 mL of methanol was slowly added to the suspension to remove water from the microspheres, and the microspheres were stirred for an additional hour. The microspheres were then filtered and washed with an additional 75 mL of methanol, filtered again, washed twice with 75 mL of ethanol and dried in a nitrogen purged vacuum oven set at 100° C. The resulting microspheres were white in color.

The diameter of the resulting dried microspheres was measured from photos acquired using scanning electron microscopy and the swell was determined as described in General Methods. The results are summarized in Table 14. In contrast to microspheres prepared using acrylamide alone (Example 25), microspheres prepared using acrylic acid and acrylamide as co-monomers had high swell.

TABLE 14

Properties of acrylic acid-acrylamide microspheres

| Example | Yield (g) | Diameter (μm) | Swell (g $H_2O$/g microsphere) |
|---|---|---|---|
| 26 | 7.93 | 30-310 | 118 |
| 27 | 8.92 | 30-245 | 78 |

Examples 28-30

Preparation of Swellable Microspheres Using Acrylic Acid and 2-Hydroxyethyl Methacrylate as Co-Monomers In three separate 1 L round-bottom, three-necked flasks, each equipped with an overhead stirrer, thermometer, reflux condenser, and nitrogen inlet port, solutions of 6.0 g of ethyl cellulose, 200 mL of chloroform, and 72 mL of methylene chloride (solution A) were prepared. Each mixture was stirred at 250 rpm until the ethyl cellulose dissolved. In a series of second flasks, three solutions of 0.25 g methyl cellulose, varying amounts of N,N'-methylenebisacrylamide to give 2.4 Mol % of total amount of monomers (as listed in Table 15), 4.335 g Triton™ X-405 (70% wt solution in water), and 25.3 g of water (solution B) were prepared. In a third series of separate flasks, varying amounts of acrylic acid and 25% aqueous sodium hydroxide solution (to reach a pH of between 5 and 6) (solution C) as given in Table 15 were mixed. To these solutions different amounts of 2-hydroxyethyl methacrylate (HEMA) were added to generate the co-monomer solutions with acrylic acid and 2-hydroxyethyl methacrylate compositions as given in Table 15. The amount of NaOH and the crosslinker were changed to accommodate the monomer ratios. Each monomer solution was then added to the appropriate solution B.

TABLE 15

Experimental conditions for preparation of acrylic acid-2-hyrdoxyethyl methacrylate microspheres

| Example | % Acrylic Acid/ % HEMA | Crosslinker (g) | Acrylic Acid (g) | NaOH (mol) | HEMA (g) | Stirring Rate (rpm) |
|---|---|---|---|---|---|---|
| 28 | 95/5 | 0.489 | 9.262 | 0.064 | 0.49 | 368 |
| 29 | 67/33 | 0.43 | 6.825 | 0.047 | 3.12 | 380 |
| 30 | 50/50 | 0.39 | 4.875 | 0.034 | 4.875 | 375 |

Then while rapidly stirring the mixtures of Solutions B and C, 0.025 g of the water-soluble azo initiator VA-044 (2,2'-azobis(2-[2-imidazolin2-yl])propane dihydrochloride) was added, and the resulting solutions were stirred for 5 min, forming the "first solutions". The first solutions were then added to the round-bottom flasks containing the appropriate solution A (the "second solutions"). The resulting reaction mixtures were stirred (see Table 15 for stirring rates) for about 1 h at room temperature, forming the "first suspensions". The stirring speed was reduced to about 225 rpm and the suspensions were heated to 51° C. with continued stirring for almost 6 h to allow for substantial microsphere formation (the "second suspensions"). The suspensions were then stirred for another 14 h at room temperature to ensure complete polymerization. After this time, approximately 250 mL of methanol was slowly added to the suspensions to remove water from the microspheres, and the microspheres were stirred for an additional hour. The microspheres were then filtered, washed with an additional 75 mL of methanol, filtered again, washed twice with 75 mL of ethanol, and dried in a nitrogen purged vacuum oven set at 100° C. The resulting microspheres were white in color.

The diameter of the resulting dried microspheres was measured from photos acquired using scanning electron microscopy and the swell was determined as described in General Methods. The results are summarized in Table 16.

TABLE 16

Properties of acrylic acid-2-hyrdoxyethyl methacrylate microspheres

| Example | Yield (g) | Diameter (μm) | Swell (g $H_2O$/g microsphere) |
|---|---|---|---|
| 28 | 8.2 | 45-230 | 112 |
| 29 | 5.7 | 15-145 | 109 |
| 30 | 4.0 | 15-190 | 174 |

Examples 31-33

Preparation of Swellable Microspheres Using Acrylic Acid and 2-Hydroxyethyl Acrylate as Co-Monomers In three separate 1 L round-bottom, three-necked flasks, each equipped with an overhead stirrer, thermometer, reflux condenser, and nitrogen inlet port, solutions of 6.0 g of ethyl cellulose, 200 mL of chloroform, and 72 mL of methylene chloride (solution A) were prepared. Each mixture was stirred at 250 rpm until the ethyl cellulose dissolved. In a series of second flasks, three solutions of 0.25 g methyl cellulose, varying amounts of N,N'-methylenebisacrylamide to give 2.4 Mol % of total amount of monomers (as listed in Table 17), 4.335 g Triton™ X-405 (70% wt solution in water), and 25.3 g of water (solution B) were prepared. In a third series of separate flasks, varying amounts of acrylic acid and 25% aqueous sodium hydroxide solution (to reach a pH of between 5 and 6) (solution C) as given in Table 17 were mixed. To these solutions different amounts of 2-hydroxyethyl acrylate (HEA) were added to generate the co-monomer solutions with acrylic acid and 2-hydroxyethyl methacrylate compositions as given in Table 17. The amount of NaOH and the crosslinker were changed to accommodate the monomer ratios. Each monomer solution was then added to the appropriate solution B.

TABLE 17

Experimental conditions for preparation of acrylic acid-2-hyrdoxyethyl acrylate microspheres

| Example | % Acrylic Acid/% HEA | Crosslinker (g) | Acrylic acid (g) | NaOH (mol) | HEA (g) | Stirring rate rpm |
|---|---|---|---|---|---|---|
| 31 | 95/5 | 0.49 | 9.262 | 0.064 | 0.49 | 370 |
| 32 | 80/20 | 0.463 | 7.8 | 0.054 | 1.95 | 325 |
| 33 | 60/40 | 0.42 | 5.85 | 0.041 | 3.9 | 327 |

Then while rapidly stirring the mixtures of Solutions B and C, 0.025 g of the water-soluble azo initiator VA-044 (2,2'-azobis(2-[2-imidazolin2-yl])propane dihydrochloride) was added, and the resulting solutions were stirred for 5 min, forming the "first solutions". The first solutions were then added to the round-bottom flasks containing the appropriate solution A (the "second solutions"). The resulting reaction mixtures were stirred (see Table 17 for stirring rates) for about 1 h at room temperature, forming the "first suspensions". The stirring speed was reduced to about 225 rpm and the suspensions were heated to 51° C. with continued stirring for almost 6 h to allow for substantial microsphere formation (the "second suspensions"). The suspensions were then stirred for another 14 h at room temperature to ensure complete polymerization. After this time, approximately 250 mL of methanol was slowly added to the suspensions to remove water from the microspheres, and the microspheres were stirred for an additional hour. The microspheres were then filtered, washed with an additional 75 mL of methanol, filtered again, washed twice with 75 mL of ethanol, and dried in a nitrogen purged vacuum oven set at 100° C. The resulting microspheres were white in color.

The diameter of the resulting dried microspheres was measured from photos acquired using scanning electron microscopy and the swell was determined as described in General Methods. The results are summarized in Table 18.

TABLE 18

Properties of acrylic acid-2-hyrdoxyethyl acrylate microspheres

| Example | Yield (g) | Diameter (μm) | Swell (g H$_2$0/g microsphere) |
|---|---|---|---|
| 31 | 4.74 | 15-180 | 148 |
| 32 | 8.17 | 45-250 | 75 |
| 33 | 8.18 | 30-230 | 97 |

Example 34

Control of Swellable Microsphere Water Uptake via Drying Conditions of Swellable Microspheres In a 5 L round-bottom, three-necked flask equipped with an overhead stirrer, thermometer, reflux condenser, and nitrogen inlet port was prepared a solution of 36.0 g ethyl cellulose, 1200 mL of chloroform, and 570 g of methylene chloride (solution A). The mixture was stirred at 100 rpm until the ethyl cellulose dissolved; then the agitator was increased in speed to 200 rpm to create a slight vortex. In a second flask, was prepared a solution of 1.50 g methyl cellulose, 3.00 g N,N'-methylenebisacrylamide (2.3 Mol % of monomer), 26.01 g of Triton™ X-405 (polyoxyethylene (40) isooctylphenyl ether—70% solution in water), and 149.4 g of water (solution B). In a third separate flask was mixed 58.5 g of acrylic acid and 75 g of a 25% aqueous sodium hydroxide solution (to reach a pH between 5 and 6) (solution C). This acrylic acid solution was then added to the water solution B.

At this point, while rapidly stirring the mixture of Solutions B and C, 0.15 g of the water-soluble azo initiator VA-044 (2,2'-azobis(2-[2-imidazolin-2-yl])propane dihydrochloride) was added, and the resulting solution was stirred for 5 min. This solution (the "first solution") was then added to the round-bottom flask containing solution A (the "second solution"). The resulting reaction mixture was allowed to stir (the "first suspension") at 200 rpm for about 1 h at room temperature. The first suspension was then heated to 51° C. and stirred at 140 rpm for an additional 10 h at that temperature to allow substantial microsphere formation (the "second suspension"). The second suspension was then stirred at 140 rpm for another 14 h at room temperature to ensure complete polymerization. After this time, approximately 1200 mL of methanol was slowly added to the second suspension to remove water from the microspheres, and the microspheres were allowed to stir for an additional hour. The microspheres were then filtered, washed with an additional 250 mL of methanol, filtered again, and finally washed with 250 mL of ethanol. A portion of the microspheres was then dried in a nitrogen purged vacuum oven set at room temperature for 144 h. The resulting microspheres were white in color. Microsphere swell was tested as described in General Methods. When exposed to water, the microspheres absorbed 120 g of water/g of microspheres.

For comparison, a second batch of microspheres produced from the procedure was dried in a nitrogen purged vacuum oven set at 100° C. for 52 h. The resulting white microspheres were tested for swell as described in General Methods. When exposed to water, the microspheres absorbed 90 g of water/g of microspheres.

These results indicate that a slow room temperature drying process leads to microspheres that exhibit a greater degree of swell than those prepared using a heated drying process.

Example 35

Preparation of Highly Swellable Microspheres

Preparation of highly swellable microspheres can be attained through the use of a highly hydrophilic monomer, such as sodium acrylate, low crosslink density, and a room temperature drying process. The following process illustrates such a preparation.

In a 5 L round-bottom, three-necked flask equipped with an overhead stirrer, thermometer, reflux condenser, and nitrogen inlet port was prepared a solution of 36.0 g ethyl cellulose, 1200 mL of chloroform, and 570 g of methylene chloride (solution A). The mixture was stirred at 100 rpm until the ethyl cellulose dissolved; then the agitator was increased in speed to 200 rpm to create a slight vortex. In a second flask, was prepared a solution of 1.50 g methyl cellulose, 0.10 g N,N'-methylenebisacrylamide (0.08 Mol % of monomer), 26.01 g Triton™ X-405 (polyoxyethylene (40) isooctylphenyl ether—70% solution in water), and 96.9 g water (solution B). In a third separate flask was mixed 58.5 g of acrylic acid and 127.5 g of a 25% aqueous sodium hydroxide solution (to reach a pH between 9 and 10) (solution C). This acrylic acid solution was then added to the water solution B.

At this point, while rapidly stirring the mixture of Solutions B and C, 0.15 g of the water-soluble azo initiator VA-044 (2,2'-azobis(2-[2-imidazolin-2-yl])propane dihydrochloride) was added, and the resulting solution was stirred for 5 min. This solution (the "first solution") was then added to the round-bottom flask containing solution A (the "second solution"). The resulting reaction mixture was allowed to stir (the "first suspension") at 200 rpm for about 1 h at room temperature. The first suspension was then heated to 51° C. and stirred at 140 rpm for an additional 10 h at that temperature to allow substantial microsphere formation (the "second suspension"). The second suspension was then stirred at 140 rpm for another 14 h at room temperature to ensure complete polymerization. After this time, approximately 1200 mL of methanol was slowly added to the second suspension to remove water from the microspheres, and the microspheres were allowed to stir for an additional hour. The microspheres were then filtered, washed with an additional 250 mL of methanol, filtered again, and finally washed with 250 mL of ethanol. A portion of the microspheres were then dried in a nitrogen purged vacuum oven set at room temperature for 64 h. The resulting microspheres were white in color. Microsphere swell was tested as described in General Methods. When exposed to water, the microspheres absorbed 269 g of water/g of microspheres. The average bulk density of these microspheres was measured to be 0.884±0.061 g/cm$^3$ (average and standard deviation of 5 determinations).

For comparison, a second batch of microspheres produced from the procedure was dried in a nitrogen purged vacuum oven set at 100° C. for 64 h. The resulting white microspheres were tested for swell as described in General Methods. When exposed to water, the microspheres absorbed 120 g of water/g of microspheres.

Total yield of microspheres (dried under both conditions) was 81.6 g. A scanning electron micrograph examination of the product beads indicated spherical size ranges from 50 microns to 250 microns.

Example 36

Preparation of Swellable Microspheres Using Styrene Sulfonic Acid

In a 1 L round-bottom, three-necked flask equipped with an overhead stirrer, thermometer, reflux condenser, and nitrogen inlet port was prepared a solution of 6.0 g of ethyl cellulose, 269 mL of chloroform, and 97 g of methylene chloride (solution A). The mixture was stirred at 244 rpm until the ethyl cellulose dissolved. In a second flask, was prepared a solution of 0.25 g methyl cellulose, 0.175 g of N,N'-methylenebisacrylamide (2.4 Mol % of monomer), 4.335 g Triton™ X-405 (polyoxyethylene (40) isooctylphenyl ether—70% solution in water), and 5.0 g of water (solution B). In a third separate flask was mixed 9.75 g of 4-styrenesulfonic acid, sodium salt hydrate (0.047 mol) and 17.24 g of a 10% HCl solution (0.047 mol; to convert the sodium salt of the monomer to the acid form), also 28.9 g of water was added to this solution (to reach a pH of 0) (solution C). The monomer solution was then added to the crosslinker solution (solution B). The total amount of water in the medium was 49.4 g, including that from the HCl. The amount of chloroform and methylene chloride were increased relative to the amounts used with acrylic acid (Example 1) in order to maintain a similar ratio of organic to water solutions.

At this point while rapidly stirring the mixture of solutions B and C, 0.025 g of the water-soluble azo initiator VA-044 (2,2'-azobis(2-[2-imidazolin2-yl])propane dihydrochloride) was added, and the resulting solution was stirred for 5 min. This solution (the "first solution") was then added to the round-bottom flask containing solution A (the "second solution"). The resulting reaction mixture was allowed to stir (the "first suspension") at 235 rpm for about 1 h at room temperature. The stirring speed was reduced to 224 rpm and the first suspension was heated to 50.3° C. The suspension was maintained at the same stirring rate and temperature for almost 6 h to allow for substantial microsphere formation (the "second suspension"). The second suspension was then stirred at 223 rpm for another 14 h at room temperature to ensure complete polymerization. After this time, approximately 250 mL of methanol was slowly added to the second suspension to remove water from the microspheres, and the microspheres were stirred an additional hour. The microspheres were then filtered, the material obtained was too soft to be isolated. The soft mass was washed with acetone and then filtered again. The material was further washed with 100 mL of methanol and washed again twice with 80 mL portions of ethanol. Finally the solids were dried in a nitrogen purged vacuum oven set at 100° C. The resulting microspheres where obtained as a fine powder with a yellow tint. The final yield of dried microspheres was 5.26 g.

The resulting dried microspheres exhibited diameters generally ranging from 10 microns to 70 microns as measured from photos acquired via scanning electron microscopy. Microsphere swell was tested as described in General Methods. When exposed to water, the microspheres absorbed 471 g of water/g of microspheres.

Example 37

Preparation of Swellable Microspheres Using Styrene Sulfonic Acid and the Sodium Salt of Styrene Sulfonic Acid In a 1 L round-bottom, three-necked flask equipped with an overhead stirrer, thermometer, reflux condenser, and nitrogen inlet port was prepared a solution of 6.0 g of ethyl cellulose, 274 g of chloroform, and 99 mL of methylene chloride (solution A). The mixture was stirred at 244 rpm until the ethyl cellulose dissolved. In a second flask, was prepared a solution of 0.25 g methyl cellulose, 0.175 g of N,N'-methylenebisacrylamide (2.4 Mol % of monomer), 4.335 g Triton™ X-405 (polyoxyethylene (40) isooctylphenyl ether—70% solution in water), and 5.0 g of water (solution B). In a third separate flask was mixed 9.75 g of 4-styrenesulfonic acid, sodium salt hydrate (0.047 mol) and 8.62 g of a 10% HCl solution (0.0236 mol; to convert 50% of the sodium salt of the monomer to the acid form), also 32.3 g of water was added to this solution (to reach a pH of 0) (solution C). The monomer solution was then added to the crosslinker solution (solution B). The total amount of water in the medium was 45.06 g, including that from the HCl. The amount of chloroform and methylene chloride were increased relative to the amounts used with acrylic acid (Example 1) in order to maintain a similar ratio of organic to water solutions.

At this point while rapidly stirring the mixture of solutions B and C, 0.025 g of the water-soluble azo initiator VA-044 (2,2'-azobis(2-[2-imidazolin2-yl])propane dihydrochloride) was added, and the resulting solution was stirred for 5 min. This solution (the "first solution") was then added to the round-bottom flask containing solution A (the "second solution"). The resulting reaction mixture was allowed to stir (the "first suspension") at 235 rpm for about 1 h at room temperature. The stirring speed was reduced to 223 rpm and the first suspension was heated to 50.4° C. The suspension was maintained at the same stirring rate and temperature for almost 6 h to allow for substantial microsphere formation (the "second suspension"). The second suspension was then stirred at 223 rpm for another 14 h at room temperature to ensure complete polymerization. After this time, approximately 250 mL of methanol was slowly added to the second suspension to remove water from the microspheres, and the microspheres were stirred an additional hour. The microspheres were then filtered, the material obtained was too soft to be isolated. The soft mass was washed with acetone and then filtered again. The material was further washed with 100 mL of methanol and washed again twice with 80 mL portions of ethanol. Finally the solids were dried in a nitrogen purged vacuum oven set at 100° C. The resulting microspheres where obtained as a fine powder with a yellow tint. The final yield of dried microspheres was 6.29 g.

The resulting dried microspheres exhibited diameters generally ranging from 30 microns to 230 microns as measured from photos acquired via scanning electron microscopy. Microsphere swell was tested as described in General Methods. When exposed to water, the microspheres absorbed 536 g of water/g of microspheres.

Example 38

Preparation of Swellable Microspheres Using the Sodium Salt of Styrene Sulfonic Acid and Acrylic Acid In a 1 L round-bottom, three-necked flask equipped with an overhead stirrer, thermometer, reflux condenser, and nitrogen inlet port was prepared a solution of 6.0 g of ethyl cellulose, 200 mL of chloroform, and 72 mL of methylene chloride (solution A). The mixture was stirred at 244 rpm until the ethyl cellulose dissolved. In a second flask, was prepared a solution of 0.25 g methyl cellulose, 0.175 g of N,N'-methylenebisacrylamide (2.4 Mol % of total monomer content: styrene sulfonic acid sodium salt hydrate and acrylic acid), 4.335 g Triton™ X-405 (polyoxyethylene (40) isooctylphenyl ether—70% solution in water), and 17.76 g of water (solution B). In a third separate flask was mixed 4.785 g of 4-styrenesulfonic acid, sodium salt hydrate (0.0236 mol), and 4.785 g of acrylic acid (0.068 mol), also 15.24 g of water was added to this solution (the solution had a pH of 1) (solution C). The monomer solution was then added to the crosslinker solution (solution B).

At this point while rapidly stirring the mix of solutions B and C, 0.025 g of the water-soluble azo initiator VA-044 (2,2'-azobis(2-[2-imidazolin2-yl])propane dihydrochloride) was added, and the resulting solution was stirred for 5 min. This solution (the "first solution") was then added to the round-bottom flask containing solution A (the "second solution"). The resulting reaction mixture was allowed to stir (the "first suspension") at 275 rpm for about 1 h at room temperature. The stirring speed was reduced to 222 rpm and the first suspension was heated to 50.4° C. The suspension was maintained at the same stirring rate and temperature for almost 6 h to allow for substantial microsphere formation (the "second suspension"). The second suspension was then stirred at 223 rpm for another 14 h at room temperature to ensure complete polymerization. After this time, approximately 250 mL of methanol was slowly added to the second suspension to remove water from the microspheres, and the microspheres were allowed to stir an additional hour. The microspheres were then filtered, the material obtained was too soft to be isolated. The soft mass was washed with acetone and then filtered again. The material was further washed with 100 mL of methanol and washed again twice with 80 mL portions of ethanol. Finally the solids were dried in a nitrogen purged vacuum oven set at 70° C. over a period of three days. The resulting microspheres where obtained as a fine powder with a yellow tint. The final yield of dried microspheres was 3.65 g.

The resulting dried microspheres exhibited diameters generally ranging from 10 microns to 95 microns as measured from photos acquired via scanning electron microscopy. Microsphere swell was tested as described in General Methods. When exposed to water, the microspheres absorbed 332 g of water/g of microspheres.

Example 39

Preparation of Swellable Microspheres Using Acrylic Acid and Poly(Ethyleneglycol)Diacrylate Crosslinker In a 1 L round-bottom, three-necked flask equipped with an overhead stirrer, thermometer, reflux condenser, and nitrogen inlet port was prepared a solution of 6.0 g of ethyl cellulose, 200 mL of chloroform, and 72 mL of methylene chloride (solution A). The mixture was stirred at 180 rpm until the ethyl cellulose dissolved. In a second flask, was prepared a solution of 0.25 g methyl cellulose, 0.838 g of poly(ethyleneglycol) diacrylate (2.4 Mol % of monomer), 4.335 g Triton™ X-405 (polyoxyethylene (40) isooctylphenyl ether—70% solution in water), and 24.9 g of water (solution B). In a third separate flask was mixed 9.75 g of acrylic acid and 10.82 g of a 25% aqueous sodium hydroxide solution (to reach a pH of between 5 and 6) (solution C). This acrylic acid solution was then added to the water solution (solution B).

At this point while rapidly stirring the mixture of solutions B and C, 0.025 g of the water-soluble azo initiator VA-044 (2,2'-azobis(2-[2-imidazolin2-yl])propane dihydrochloride) was added, and the resulting solution was stirred for 5 min. This solution (the "first solution") was then added to the round-bottom flask containing solution A (the "second solution"). The resulting reaction mixture was allowed to stir (the "first suspension") at 327 rpm for about 1 h at room temperature. The stirring speed was reduced to 224 rpm and the first suspension was heated to 50.4° C. The suspension was maintained at the same stirring rate and temperature for almost 6 h to allow for substantial microsphere formation (the "second suspension"). The second suspension was then stirred at 225 rpm for another 14 h at room temperature to ensure complete polymerization. After this time, approximately 250 mL of methanol was slowly added to the second suspension to remove water from the microspheres, and the microspheres were stirred for an additional hour.

The resulting microspheres clumped together at the bottom of the reaction flask into a big mass which was difficult to separate into individual microspheres. A small portion of the collected microsphere mass was removed using tweezers. Various solvents including acetone, methanol, ethanol and hexane were utilized to test if the portion could be separated into individual microspheres. The individual microspheres were observed under a desk optical microscope. Eventually, it was found that water was able to dissolve the beads.

What is claimed is:

1. A process for making a microsphere preparation, comprising:
   a) forming a first solution comprising:
     (i) water;
     (ii) at least one water miscible monomer selected from the group consisting of acrylic acid, methacrylic acid, salts of acrylic acid and methacrylic acid, acrylamide, methacrylamide, N-substituted acrylamides, N-substituted methacrylamides, 2-acryloylethane-sulfonic acid, 2-methacryloylethane-sulfonic acid, salts of 2-acryloylethane-sulfonic acid, and 2-methacryloylethane-sulfonic acid, styrene-sulfonic acid, salts of styrene-sulfonic acid, 2-hydroxyethyl acrylate, and 2-hydroxyethyl methacrylate, provided that:
       (A) if said monomer is acrylamide, methacrylamide, N-substituted acrylamides, 2-hydroxyethyl acrylate, or 2-hydroxyethyl methacrylate, said monomer is used in combination with at least one other monomer selected from subgroup 1 consisting of:

acrylic acid, methacrylic acid, salts of acrylic acid and methacrylic acid, 2-acryloylethane-sulfonic acid, 2-methacryloylethane-sulfonic acid, salts of 2-acryloylethane-sulfonic acid and 2-methacryloylethane-sulfonic acid, styrene-sulfonic acid, and salts of styrene-sulfonic acid;

(B) if said first solution contains at least one monomer from subgroup 2 consisting of acrylic acid, methacrylic acid, salts of acrylic acid and methacylic acid, acrylamide, methacrylamide, N-substituted acrylamides, N-substituted methacrylamides, 2-hydroxyethyl acrylate, and 2-hydroxyethyl methacrylate, but does not contain a monomer selected from subgroup 3 consisting of 2-acryloylethane-sulfonic acid, 2-methacryloylethane-sulfonic acid, salts of 2-acryloylethane-sulfonic acid and 2-methacryloylethane-sulfonic acid, styrene-sulfonic acid, and salts of styrene-sulfonic acid, then the pH of the first solution is at least 3 or about 3;

(C) if said first solution contains at least one monomer from subgroup 3 consisting of 2-acryloylethane-sulfonic acid, 2-methacryloylethane-sulfonic acid, salts of 2-acryloylethane-sulfonic acid and 2-methacryloylethane-sulfonic acid, styrene-sulfonic acid, and salts of styrene-sulfonic acid, then the pH of the first solution is less than 3 or about 3;

(iii) a crosslinking agent that is miscible in the first solution in less than 5 or equal to about 5 mol %, relative to total moles of monomer and crosslinking agent, said crosslinking agent being selected from the group consisting of N,N'-methylene-bis-acrylamide, N,N'-methylene-bis-methacrylamide, N-methylolacrylamide, N-methylolmethacrylamide, glycidyl acrylate, glycidyl methacrylate, polyethylene glycol diacrylate, polyethylene glycol dimethacrylate, polyvalent metal salts of acrylic acid and methacrylic acid, divinyl benzene phosphoacrylates, divinylbenzene, divinylphenylphosphine, divinyl sulfone, 1,3-divinyltetramethyldisiloxane, 3,9-divinyl-2,4,8,10-tetraoxaspiro[5,5]undecane, phosphomethacrylates, ethylene glycol diglycidyl ether, glycerin triglycidyl ether, glycerin diglycidyl ether, and polyethylene glycol diglycidyl ether;

(iv) a water soluble protecting colloid;

(v) an emulsifier; and (vi) a low temperature aqueous soluble azo initiator;

b) forming a second solution comprising at least one substantially chlorinated hydrocarbon of less than 6 carbon units, provided that the chlorinated hydrocarbon is not a halogenated aromatic hydrocarbon, and an organic soluble protecting colloid;

c) forming a first suspension with agitation comprising the first and second solutions at a temperature below the initiation temperature of the azo initiator of (a);

d) increasing the temperature of the agitating first suspension to a temperature at which the low temperature aqueous soluble azo initiator is activated;

e) agitating the first suspension until it forms a second suspension comprising a gelatinous precipitate suspended in an organic liquid phase, wherein microspheres are formed;

f) allowing the second suspension to cool to a temperature that is at about 30° C. or below 30° C. while agitating the second suspension;

g) washing the second suspension at least once with a dehydrating solvent wherein water is removed from the microspheres forming a microsphere preparation; and h) recovering the microsphere preparation.

2. A process according to claim 1 wherein the second solution comprises a mixture of methylene chloride and chloroform.

3. A process according to claim 1 wherein the second solution comprises a combination of methylene chloride and a solvent or solvent mixture having a sum of differences in Hansen solubility parameters relative to the Hansen solubility parameters of chloroform of less than 0.21 or about 0.21.

4. A process according to claim 3 wherein the solvent mixture is selected from the group consisting of: 20 vol % methyl oleate:80 vol % phenethyl acetate, 30 vol % ethyl heptanoate:70 vol % phenethyl acetate, 30 vol % methyl octanoate:70 vol % phenethyl acetate, 40 vol % diethyl carbonate:60 vol % methylphenyl acetate, 20 vol % phenylpropyl methyl ether:80 vol % phenyl propyl ether, 70 vol % ethyl phenyl ether:30 vol % phenylpropyl methyl ether, 20 vol % diethylene glycol butyl ether:80 vol % phenylpropyl methyl ether, 20 vol % ethyl propionate:80 vol % phenylpropyl acetate, 80 vol % phenylpropyl acetate:20 vol % tripropylamine, 90 vol % phenyl propyl ether:10 vol % toluene, 30 vol % methyl hexanoate:70 vol % phenylpropyl acetate, and 20 vol % isopropyl palmitate:80 vol % phenethyl acetate.

5. A process according to claim 1 wherein the first solution further comprises a barium monomer salt.

6. A process according to claim 1 wherein the azo initiator of (a) has an initiation temperature that is less than 53 ° C.

7. A process according to claim 6 wherein the azo initiator is 2,2'-azobis (2-[2-imidazolin-2-yl])propane dihydrochloride.

8. A process according to claim 1 wherein the protecting colloid of (a) is a water soluble cellulose ester or ether.

9. A process according to claim 8 wherein the protecting colloid is methyl cellulose.

10. A process according to claim 1 wherein the protecting colloid of (b) is an organic soluble cellulose ester or ether.

11. A process according to claim 10 wherein the protecting colloid is ethyl cellulose.

12. A process according to claim 1 wherein the emulsifier of (a) is a nonionic surfactant.

13. A process according to claim 12 wherein the emulsifier is an alkylaryl polyether alcohol preparation.

14. A process according to claim 1 wherein the first suspension of (c) is formed at a temperature below 30° C. or about 30° C.

15. A process according to claim 1 wherein the temperature in (d) is between about 50° C. and 55° C.

16. A process according to claim 1 wherein the monomer is a combination comprising acrylic acid and at least one monomer selected from the group consisting of: sodium acrylate, acrylamide, 2-hydroxyethyl methacrylate, 2-hydroxyethyl acrylate, styrene sulfonic acid, and sulfonic acid sodium salt.

17. A process according to claim 1 wherein the monomer is styrene sulfonic acid or a combination comprising styrene sulfonic acid and styrene sulfonic acid sodium salt.

18. A process according to claim 1 wherein the crosslinking agent is N,N'-methylenebisacrylamide.

19. A process according to claim 1 wherein the crosslinking agent is present in the first solution at about 0.08 mol % to about 4 mol % relative to the total moles of monomer and crosslinking agent.

20. A process according to claim 1 further comprising drying the recovered microsphere preparation.

21. A process according to claim 20 wherein the drying is at about 20° C. to about 25° C. under vacuum with a nitrogen purge.

22. A process for making a microsphere preparation, comprising:
- a) forming a first solution having a pH of between about 5 and about 9 comprising:
  - (i) water;
  - (ii) a combination comprising acrylic acid and at least one monomer selected from the group consisting of sodium acrylate, acrylamide, 2-hydroxyethyl methacrylate, and 2-hydroxyethyl acrylate;
  - (iii) N,N'-methylenebisacrylamide crosslinking agent in about 0.08 mol % to about 2.3 mol %, relative to total moles of monomer and crosslinking agent;
  - (iv) methyl cellulose protecting colloid;
  - (v) an alkylaryl polyether alcohol preparation as emulsifier, and
  - (vi) 2,2'-azobis(2- [2-imidazolin-2-yl])propane dihydrochloride azo initiator;
- b) forming a second solution comprising a combination of methylene chloride and chloroform, or methylene chloride and a mixture of 30 vol % ethyl heptanoate:70 vol % phenethyl acetate; in a volume ratio that is between about 1:5 and 5:1, and ethyl cellulose as an organic soluble protecting colloid;
- c) forming a first suspension with agitation comprising the first and second solutions at a temperature of about 25° C.;
- d) increasing the temperature of the agitating first suspension to a temperature of about 51° C. to 52° C. wherein the 2,2'-azobis(2-[2-imidazolin-2-yl])propane dihydrochloride azo initiator is activated;
- e) agitating the first suspension until it forms a second suspension comprising a gelatinous precipitate suspended in an organic liquid phase, wherein microspheres are formed;
- f) allowing the second suspension containing microspheres to cool to a temperature of about 25° C. while agitating the second suspension;
- g) washing the second suspension twice with methanol, followed by once with ethanol wherein water is removed from the microspheres forming a microsphere preparation;
- h) recovering the microsphere preparation; and
- i) drying the microsphere preparation to form a free-flowing microsphere powder.

23. A process for making a microsphere preparation, comprising:
- a) forming a first solution having a pH of less than 3 or about 3 comprising:
  - (i) water;
  - (ii) styrene sulfonic acid or a combination comprising styrene sulfonic acid and styrene sulfonic acid sodium salt;
  - (iii) N,N'-methylenebisacrylamide crosslinking agent in about 0.08 mol % to about 2.3 mol %, relative to total moles of monomer and crosslinking agent;
  - (iv) methyl cellulose protecting colloid;
  - (v) an alkylaryl polyether alcohol preparation as emulsifier, and
  - (vi) 2,2'-azobis(2-[2-imidazolin-2-yl])propane dihydrochloride azo initiator;
- b) forming a second solution comprising a combination of methylene chloride and chloroform, or methylene chloride and a mixture of 30 vol % ethyl heptanoate:70 vol % phenethyl acetate; in a volume ratio that is between about 1:5 and 5:1, and ethyl cellulose as an organic soluble protecting colloid;
- c) forming a first suspension with agitation comprising the first and second solutions at a temperature of about 25° C.;
- d) increasing the temperature of the agitating first suspension to a temperature of about 51° C. to 52° C. wherein the 2,2'-azobis (2-[2-imidazolin-2-yl])propane dihydrochloride azo initiator is activated;
- e) agitating the first suspension until it forms a second suspension comprising a gelatinous precipitate suspended in an organic liquid phase, wherein microspheres are formed;
- f) allowing the second suspension containing microspheres to cool to a temperature of about 25° C. while agitating the second suspension;
- g) washing the second suspension twice with methanol, followed by once with ethanol wherein water is removed from the microspheres forming a microsphere preparation;
- h) recovering the microsphere preparation; and
- i) drying the microsphere preparation to form a free-flowing microsphere powder.

* * * * *